(12) United States Patent
Gale et al.

(10) Patent No.: US 8,210,119 B2
(45) Date of Patent: Jul. 3, 2012

(54) SPOTTING DEVICE AND METHOD FOR HIGH CONCENTRATION SPOT DEPOSITION ON MICROARRAYS AND OTHER MICROSCALE DEVICES

(75) Inventors: Bruce Gale, Taylorsville, UT (US); David Chang-Yen, West Jordan, UT (US); David Myszka, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 1054 days.

(21) Appl. No.: 11/632,086

(22) PCT Filed: Jul. 6, 2005

(86) PCT No.: PCT/US2005/023895
§ 371 (c)(1),
(2), (4) Date: Apr. 24, 2007

(87) PCT Pub. No.: WO2006/014460
PCT Pub. Date: Feb. 9, 2006

(65) Prior Publication Data
US 2007/0231458 A1    Oct. 4, 2007

Related U.S. Application Data

(60) Provisional application No. 60/585,697, filed on Jul. 6, 2004.

(51) Int. Cl.
*B05C 1/06* (2006.01)
(52) U.S. Cl. ... 118/256; 422/100; 347/185; 219/121.64; 118/200

(58) Field of Classification Search ............... 422/100; 219/121.64; 347/85; 118/200, 256
See application file for complete search history.

(56) References Cited

U.S. PATENT DOCUMENTS

| | | | |
|---|---|---|---|
| 3,974,508 A | | 8/1976 | Blumenthal |
| 5,847,356 A | * | 12/1998 | Santhanam ............ 219/121.64 |
| 6,110,426 A | | 8/2000 | Shalon et al. |
| 6,309,891 B1 | | 10/2001 | Shalon et al. |
| 6,365,349 B1 | | 4/2002 | Moynihan et al. |
| 6,391,625 B1 | | 5/2002 | Park et al. |

(Continued)

FOREIGN PATENT DOCUMENTS
JP    11281534 A    10/1999
(Continued)

OTHER PUBLICATIONS

PCT Preliminary Report on Patentability and Written Opinion, PCT/US2005/023895, dated Jan. 9, 2007.

*Primary Examiner* — Dah-Wei Yuan
*Assistant Examiner* — Andrew Bowman
(74) *Attorney, Agent, or Firm* — Thorpe North & Western LLP

(57) ABSTRACT

Disclosed is a spotter device and methods for the formation of microassays, biochips, biosensors, and cell cultures. The spotter may be used to deposit highly concentrated spots of protein or other materials on a microarray a slide, wafer, or other substrate. The spotter uses microfluidic conduits and orifices to deposit proteins, other biomolecules, or chemicals on a spot on a substrate. Each orifice is part of a fluid pathways that includes an inlet and outlet conduit. When the spotter contacts a substrate a seal is formed between the orifices and the substrate.

13 Claims, 10 Drawing Sheets

U.S. PATENT DOCUMENTS

| | | | |
|---|---|---|---|
| 6,503,715 | B1 | 1/2003 | Gold et al. |
| 6,511,850 | B1 | 1/2003 | Vigh et al. |
| 6,594,432 | B2 | 7/2003 | Chen et al. |
| 6,623,696 | B1 | 9/2003 | Kim et al. |
| 6,656,740 | B1 | 12/2003 | Caren et al. |
| 6,699,719 | B2 | 3/2004 | Yamazaki et al. |
| 6,703,203 | B2 | 3/2004 | Shao et al. |
| 6,733,968 | B2 | 5/2004 | Yamamoto et al. |
| 6,835,352 | B2 * | 12/2004 | Ito et al. ................. 422/100 |
| 6,994,429 | B1 * | 2/2006 | McEntee et al. ............ 347/85 |
| 2002/0028160 | A1 | 3/2002 | Xiao et al. |
| 2002/0179447 | A1 | 12/2002 | Sundberg et al. |
| 2003/0068253 | A1 | 4/2003 | Bass et al. |
| 2003/0099577 | A1 | 5/2003 | Renaud et al. |
| 2004/0014102 | A1 | 1/2004 | Chen et al. |

FOREIGN PATENT DOCUMENTS

| | | |
|---|---|---|
| JP | 2004-101480 | 4/2004 |
| JP | 2004-518106 | 6/2004 |
| JP | 2004-538446 | 12/2004 |
| WO | WO 01/74490 | 10/2001 |
| WO | WO 02/075280 | 9/2002 |

* cited by examiner

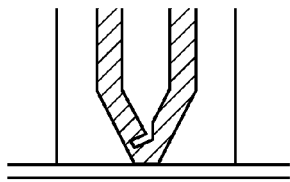
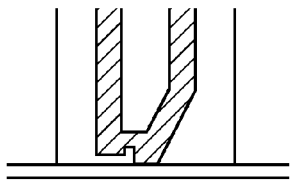
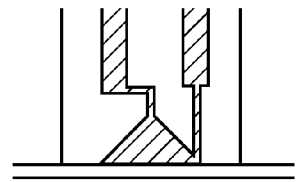
*FIG. 8A*  *FIG. 8B*  *FIG. 8C*
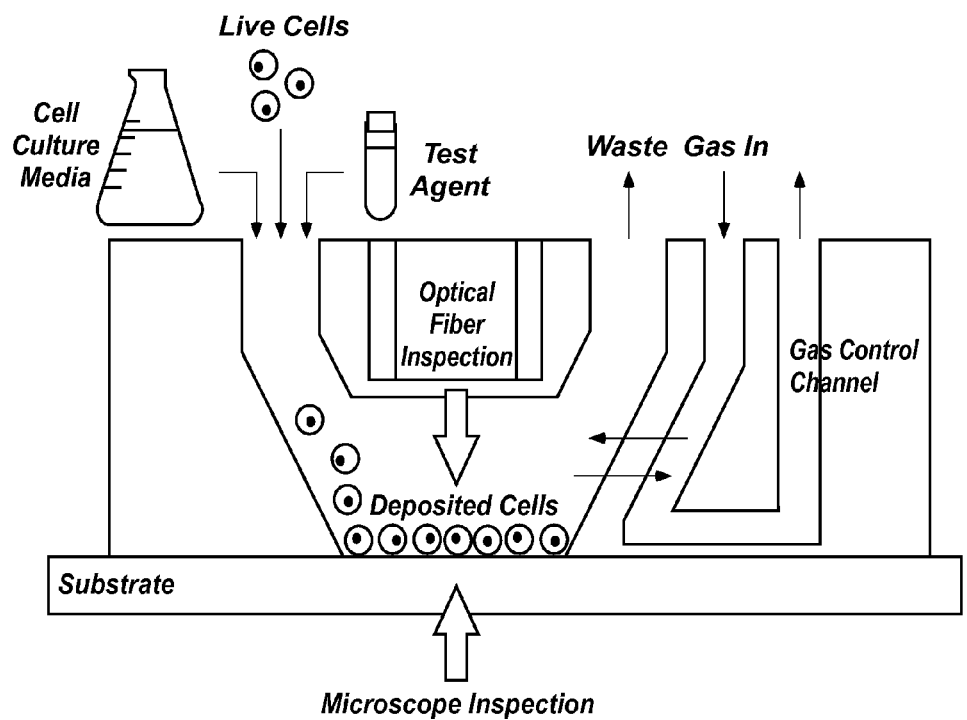
*FIG. 9*
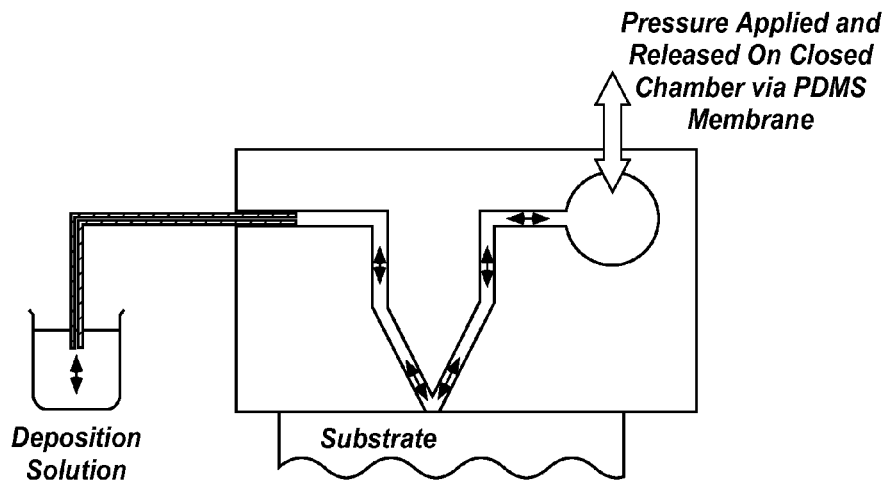
*FIG. 10*

SPOTTING DEVICE AND METHOD FOR HIGH CONCENTRATION SPOT DEPOSITION ON MICROARRAYS AND OTHER MICROSCALE DEVICES

PRIORITY CLAIM

This application claims the benefit under 35 U.S.C. § 119 (e) to U.S. Provisional Patent Application No. 60/585,697, filed on Jul. 6, 2004, the entirety of which is incorporated by reference.

TECHNICAL FIELD

The present invention relates generally to biotechnology, more specifically to building microassays, biochips, and biosensors. In particular, the present invention encompasses a system of microfluidic channels for the deposition of a substance on a substrate.

BACKGROUND

In recent years, a large number of biological/chemical analysis techniques have been demonstrated using microscale systems and have been implemented using micromachining technology. The rationale for using microscale technologies in analytical instrumentation includes reduction in instrument size and cost, reduction in sample and reagent volume, reduction in analysis time, increase in analysis throughput, and the possibility of integration of sample preparation and analysis functions.

Currently, high spot density arrays are produced using robotic spotter systems, such as the GENETIX QARRAY®. One of the current techniques uses spotting "pens" which collect the material to be deposited on a needle and then "spots" the material on to the substrate. See, e.g., U.S. Pat. No. 6,733,968 to Yamamoto et al., ("'968 patent") entitled "Microarray, Method for Producing the Same, and Method for Correcting Inter-Pin Spotting Amount Error of the Same." The '968 patent notes that when multiple "pens" are used to create an array, not all of the "pens" are microscopically the same size, and therefore each "pen" blots a different amount of solution. The patent discloses a method for determining what the errors are for a given set of "pens" so the errors can be mathematically accounted for.

U.S. Pat. No. 6,365,349 to Moynihan et al., entitled "Apparatus and Methods for Arraying Solution onto a Solid Support," discloses the use of a spring probe to administer samples onto a substrate.

Similar to the use of "pens" is the use of capillaries. See e.g., U.S. Patent Application 20040014102, Chen et al., entitled "High Density Parallel Printing of Microarrays." The application discloses the use of capillaries to spot samples onto a microarray. U.S. Pat. No. 6,594,432 to Chen et al. ("'432 patent"), entitled "Microarray Fabrication Techniques and Apparatus," also discloses the use of capillaries, such as silica tubes, to spot probes onto a substrate. In the '432 patent, one end of the capillaries may be attached to a reservoir; however there is no return path for the substance that is spotted and therefore no way to flow a substance over a substrate to increase the spot deposition density. The capillary action of the '432 patent is therefore similar to that done with pens. For an additional example see, U.S. Pat. No. 6,110,426 to Shalon et al., entitled "Methods for Fabricating Microarrays of Biological Samples," which discloses a method for tapping a meniscus at the end of a capillary tube to deliver a specified amount of sample material onto a substrate.

While prior art systems are capable of producing multiple spots of a controlled size, if the desired molecule for deposition is present in very low concentration, the total number of desired molecules that can be deposited on the surface is severely limited for a single spot. The concentration of material in the spots is limited by the concentration of the original material and the spot size. The Perkin-Elmer BIOCHIP ARRAYER® uses "ink jet printing" technology, but that method has the same concentration limitation as the "pens."

Other systems have been developed which use microfluidic channels on a substrate to pattern genes, proteins, nucleic acids, such as RNA, DNA, oligonucleic acids, or other arrays. For an example of such a system see, U.S. Pat. No. 6,503,715 to Gold et al., entitled "Nucleic Acid Ligand Diagnostic Biochip." Biochip fabrication methods have been developed that attempt to stir individual microassay spots; however, such systems often require mechanical manipulation of the biochip. See e.g., U.S. Pat. No. 6,623,696 to Kim et al., entitled "Biochip, Apparatus for Detecting Biomaterials Using the Same, and Method Therefor," which discloses spinning a biochip in order to accelerate reaction time. A need exists to simplify the process of developing biochips and biosensors and for providing more control over individual spots on the biochips and biosensors.

Ideally, a flow deposition system could produce a high surface density if the substrate surface were tailored to bond only to the desired molecules, allowing the unwanted bulk material to be washed away. However, flow deposition systems generally are incapable of producing spot arrays, let alone individually addressed arrays. See, e.g., Japan Patent Application 10084639, Tomoko et al., entitled "Method and Apparatus for Adding Sample." That application discloses a method wherein a biochip is rotated and centrifugal forces are used to uniformly spread a sample over the entire surface of the biochip. Similarly, U.S. Pat. No. 6,391,625 to Park et al., entitled "Biochip and Method for Patterning and Measuring Biomaterial of the Same," discloses a method for making biochips via irradiating portions of the substrate with a laser and then spin coating probe molecules onto the substrate.

Additionally, current technology is unable to sequentially chemically process individual spots, or to perform layer-by-layer self-assembly (LBL) to build up the spot concentration. What is needed is a way to take molecules in a solution and adhere a high-concentration of those molecules on a substrate. This would be particularly advantageous in studying protein function.

Additionally, microarray-type structures are used in forming biosensors and the same problems associated with biochips apply to biosensors. See e.g., U.S. Pat. No. 6,699,719 to Yamazaki et al., entitled "Biosensor Arrays and Methods," which discloses using microarray forming techniques in the formation of a biosensor. A need exists to simplify the creation the biosensors.

A need exists to decrease the cost and time involved in processing microarrays as well. Attempts have been made to address that need, see e.g., U.S. Patent Application 2003/0068253 A1, Bass et al., entitled "Automation-Optimized Microarray Package," which discloses a method for automating microarray processing via a linear strip of microarrays that is processed in an assembly line fashion.

DISCLOSURE OF THE INVENTION

Disclosed is a spotter capable of patterning the surface of microarrays with individually addressed high-concentration spots and methods of using and fabricating the spotter. The spotter increases the surface density at each spot by directing a flow of the desired substance, such as probes and/or target compounds, over the spot area until a high-density spot has been created. Examples of probes that may be flowed over a surface include: proteins; nucleic acids, including deoxyribonucleic acids (DNA) and ribonucleic acids (RNA); cells; peptides; lectins; modified polysaccharides; synthetic composite macromolecules; functionalized nanostructures; synthetic polymers; modified/blocked nucleotides/nucleosides; synthetic oligonucleotides; modified/blocked amino acids; fluorophores; chromophores; ligands; chelates; haptens; drug compounds; antibodies; sugars; lipids; liposomes; tissue; viruses; any other nano- or microscale objects; and any combinations thereof. As a substance flows over the surface of the microarray substrate, it can may bind or adsorb to a surface of the substrate, depending on the chemistry involved in the system.

Conduits, such as microchannels and/or microtubules, within the spotter are used to guide the substance(s) to and from the area of spot deposition on the substrate, wherein the flow through the microchannel or microtubules produces a high surface concentration in a specific region. Each deposition region may be individually addressed with its own microfluidic channel, which microfluidic channels may be assembled such that a large-number of deposition regions may be addressed in parallel. An orifice in the microfluidic channel is adapted to form a seal with a surface of the substrate, such that a solution in the microfluidic channel contacts the surface, allowing deposition of substances in the solution on the surface. The solution may be injected into an inlet of a first conduit, flowed to the deposition spot area via a first microfluidic channel to the orifice, and then flowed out through a second conduit.

In one embodiment, the first and second conduits may be connected to the same reservoir, thereby allowing recycling of the solution and any solute contained therein.

In another embodiment, the first conduit of a microfluidic channel is connected a first reservoir and the second conduit of the microfluidic channels connected to a second reservoir. A plurality of microfluidic channels may be configured such that the first conduit of each microfluidic channel is connected to a common first reservoir and the second conduit of each microfluidic channel is connected to a common second reservoir. In another embodiment, each individual first and second conduit of a microfluidic channel is connected to a separate first and second reservoir.

In one embodiment, constant fluid flow of a solution containing a substance to be deposited is maintained for an extended period to facilitate surface deposition, forming a high-density spot. This embodiment allows the user to control for decrease binding efficiency of a solute to the surface, thereby forming an array having much higher signal (e.g., when using fluorescence, chemiluminescence, color-staining, other optically-based microarray sensing technologies, or radiometrics). In another embodiment, at least 10 microfluidic channels per $cm^2$ are configured to produce a print head capable of producing individually addressed deposition sites (spots) on a surface. The 2-dimensional arrangement of the spots means that deposition can be formed on an unlimited number of spots simultaneously with different deposition materials, with each spot area positioned arbitrarily (not necessarily in a grid formation) or non-arbitrarily on the surface, and each spot area may be a different size and/or shape or the same size and/or shape.

In another embodiment, thermoregulatory elements or gas diffusion elements are adapted to contact one or more microfluidic pathways, and may be used to control the temperature of a solution in the proximity of the surface. In yet another embodiment, the flow channels (e.g., microfluidic pathways) may incorporate fluid mixing structures over the spot area, such as vortex inducers to convectively enhance the surface deposition.

In another embodiment, the spotter may be used to perform layer-by-layer self-assembly (LBL) in the assembly of a deposition site. For example, multiple layers of substances, either the same substance or a different substance, may be produced simply by changing the solution (solute) that is flowed over the spot. In one embodiment, a nucleic acid is deposited in a first layer and a DNA-bind protein is deposited in a second layer or step. In another embodiment, the surface of the substrate may be modified by flowing an appropriate material through the spotter to contact the surface. The spotter and microfluidic pathways may be fabricated from a large number of materials, and therefore, the fabrication material is preferably non-reactive with a solution to be flowed through or used in connection with the operation of the spotter.

The spotted array produced by the system disclosed herein may be applied to a surface that is subsequently embedded into a micro total analysis system (µTAS) [1], which allows the array's exposure to fluids to be precisely controlled with microchannels. Such systems that use microchannels on a substrate to pattern genes, proteins, nucleic acids (e.g., RNA, DNA, polynucleic acids), or other substances (e.g., cells, lipids, sugars, and other biomolecules assembled in array formats), can be adapted to operate with the spotter instead. This embodiment eliminates the need to build microcanals into the substrate, thereby greatly simplifying the fabrication process and reducing overall cost. The spotter may be used for fluid loading into other microfluidic systems, simply by pressing the spotter face against a surface port array. The spotter may also be used to build and test biosensors. The spotter may also be used to deposit, grow, and maintain cell cultures.

The spotter may also be used with uneven surfaces on a substrates, for example, substrates with structures built into the surface. The spotter may be designed to mate with rigid or flexible substrates that are porous or nonporous. The substrates may be made from any number of materials known in the art. The spotter face may be modified as necessary to mate with any of the various substrates.

Spot size and geometry may be varied by altering the size and geometry of the orifices during fabrication of the spotter. Spot conditions may be varied depending on the design of the spotter. For example, the orifice can be altered during fabrication to include constrictions and turbulence inducers. Flow within the spotter may be controlled numerous ways, for example, via pressure flow, electrokinetics, gravity flow, osmotic pressure, or combinations thereof.

The spotter may be fabricated out of any suitable material that is compatible with the substances to be flowed through the spotter, examples of materials include, but are not limited to: silicon; silica; polydimethylsiloxane (PDMS); gallium arsenide; glass; ceramics; quartz; polymers such as neoprene, Teflon™, polyethylene elastomers, polybutadiene/SBR, nitrites, nylon; metals, and combinations thereof. It may be desirable to build the spotter out of material for which the substances to be flowed (e.g., a solute) have a low affinity for, thus, reducing binding of the substance within the spotter microchannels. Additionally, the inner diameter of the conduits may be coated with suitable material to reduce the affinity between the substances being flowed and the conduits themselves.

The spotter may be fabricated in numerous ways, for example, by cleaning a wafer of suitable material, priming the wafer if necessary, adding material to the wafer via casting, molding, oxidation, deposition, or any other suitable method, subtracting material via machining, grinding, or etching or some other suitable method. Optionally, additional wafers may be bonded to a first wafer, and additional material may be added or subtracted as necessary, or a combination of additional wafers and materials may be added as necessary to fabricate the spotter. As will be recognized by a person of ordinary skill in the art, the fabrication steps may be performed in any order necessary to produce the desired spotter.

Additional fabrication methods are also possible, for example, rather than using semiconductor fabrication methods, a mold with stainless steel microwires may also be used. After an appropriate material has set, the microwires may be removed with the resulting voids forming microchannels. Alternatively, a mold may be used to form the spotter face and the accompanying orifices and/or microtubules, optionally, microtubules or microchannels may be mated to the back side of a molded spotter face or print head. In one exemplary embodiment, the spotter is fabricated almost entirely from microtubules. There are a wide variety of semiconductor fabrication techniques known in the art that may be used with a variety of materials, such as silica, to create, modify, and join microtubules to create a spotter with an array of orifices. A spotter produced with larger microtubules may not require fabrication, for example, using semiconductor fabrication methods, and instead may simply be secured together.

The present invention has the potential to produce microarrays with a virtually unlimited number of defined spots, with each spot individually tailored for certain substances and a specific deposition density. The spotter may also be used to sequentially chemically process individual spots, preferably through the use of the same spotter, however, multiple spotters may also be used.

BRIEF DESCRIPTION OF THE DRAWINGS

FIG. 8A is an illustration of a microchannel with an enhanced-mixing vane.
FIG. 8B is an illustration of a microchannel with an enhanced-mixing step.
FIG. 8C is an illustration of a microchannel forming a prism mold with lateral injector and vertical vent.
FIG. 9 illustrates a spotter for spotting and maintaining cell cultures.
FIG. 10 illustrates a spotter with a flexible membrane.

FIGS. 15, and 19-24 illustrate one of numerous methods of photolithographically forming a spotter.
FIG. 19 is an illustration of spin coating a photoresist on a wafer.
FIG. 20 is an illustration of exposing the photoresist.
FIG. 21 is an illustration of mold surface modification.
FIG. 22 is an example of removing a cast from a mold.
FIG. 23 illustrates one method of fluidic port coring.
FIG. 24 illustrates a method of channel sealing.

BEST MODE(S) FOR CARRYING OUT THE INVENTION

Figure 1:
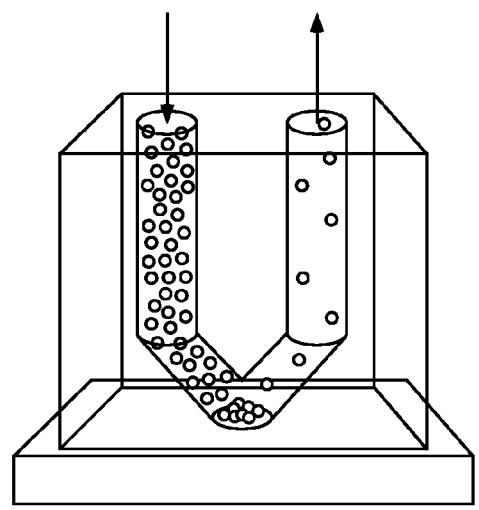
FIG. 1 is an illustration of a single orifice spotter.

Disclosed is a spotter capable of patterning the surface of microarrays with a high-concentration of individually addressed spots and methods of using and fabricating the spotter. The fluid channel of the present invention may be used to increase the surface density at each spot by directing a flow of a solution bearing a desired substance, such as probe and/or target molecules, over the spot area until a desired surface deposition density is accomplished. As used herein, the term "substance" includes probes, target compounds, cells, nutrients, and/or carriers. Examples of "probes" include: proteins; nucleic acids, including deoxyribonucleic acids (DNA) and ribonucleic acids (RNA); cells; peptides; lectins; modified polysaccharides; synthetic composite macromolecules, functionalized nanostructures; synthetic polymers; modified/blocked nucleotides/nucleosides; synthetic oligonucleotides; modified/blocked amino acids; fluorophores; chromophores; ligands; receptors; chelatores; haptens; drug compounds; antibodies; sugars; lipids; liposomes; cells; viruses; any nano- or microscale objects; and any chemical compounds that have associated substances which binds, associates, or interacts with other probe materials. Target compounds are typically flowed over probes or combinations of probes already bound to a substrate. "Carrier" refers to a vehicle for transporting probes, cells, target compounds, or nutrients. "Carriers" includes solvents (e.g., any aqueous or non-aqueous fluid and/or gel), and may have particles suspended therein.

1.0 Structure

The spotter comprises a plurality of fluid pathways, wherein a fluid pathway comprises a first conduit and a second conduit, the first and second conduit each having a proximal and a distal end, the first conduit having a wall defining a first channel in the first conduit, the second conduit having a wall defining a second channel in the second conduit, wherein the distal end of the first conduit is operably connected to the distal end of the second conduit, wherein the distal end of the first and/or second conduit are configured to produce an orifice, and wherein the orifice is operable to form a seal with a surface; the plurality of the orifices configured in a static array adapted to dispose fluid on the surface of a substrate. The fluid pathways are configured such that a fluid may flow through the first and second conduits, contacting the surface of a substrate, when the orifice is sealed against the surface.

Conduits may also be referred to as channels, microchannels, canals, microcanals, microtubules, tubules and/or tubes, where the terms are used to describe a fluid pathway. The term "inlet conduit," "inlet microchannel," or "inlet microtubule" may be either the first or second conduit and the terms "outlet conduit," "outlet microchannel," or "outlet microtubule" may be the alternative conduit of the pathway. In some embodiments, which conduit is the inlet conduit varies as a substance flows back and forth between the conduits. For the purpose of describing the invention, "inlet" or "outlet" is may be used to reference the proximal end of the respective conduit.

1.1 Conduits

Figure 2:
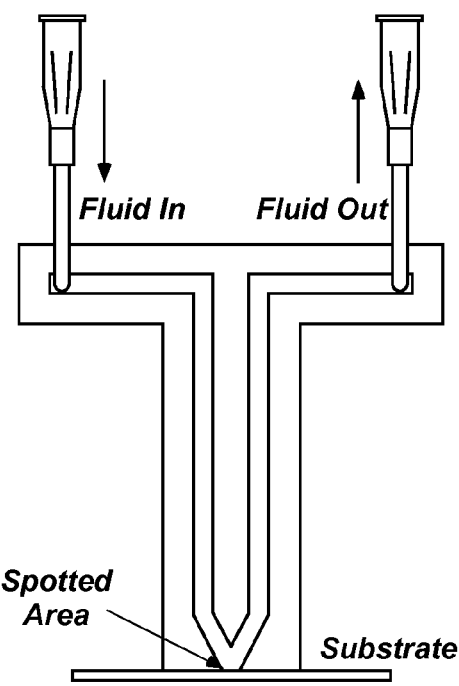
FIG. 2 is an illustration of a single orifice spotter.
Figure 3:
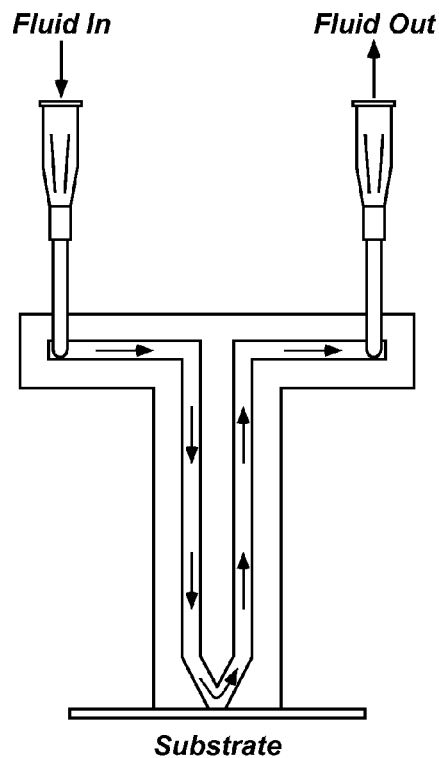
FIG. 3 is an illustration of a single orifice spotter.

FIGS. 1-3 illustrate two microchannels within a spotter for guiding substances to and from the spot deposition area on the surface of the substrate. As used herein, the "spot deposition area" is also referred to as the "spot," "spotted area" and/or the "well." A substance flows through the inlet microchannel in the spotter, to the orifice, contacting the surface of the substrate, and the through the outlet microchannel in the spotter. This flow path provides an opportunity for substances to bind or adsorb to the surface depending on the chemistry involved in the system. As used herein, the term "bind" refers to binding, adhesion, adsorption, association, or any other chemical or mechanical process for retaining a substance at a substrate. Specific binding is used to refer to a substance, such as a protein, being binding to a surface in a non-random fashion. Non-specific binding refers to undesirable binding or adhesion, as understood in the art.

As will be apparent in light of the present disclosure, the inlet and outlet (first and second) conduits may be essentially a single curved channel with a hole (orifice) in the channel for depositing substances on the substrate. However, for the purpose of describing the present invention, instead of referring to these embodiments as having a single channel or conduit, a "set" or "pair" of conduits is used to describe the channel with the orifice typically providing the division point. As discussed herein, a wide variety of connections between a set of channels (e.g., microchannels), and a wide variety of means for forming an orifice, are possible.

In one embodiment, each channel or fluid pathway of the spotter comprises a means for conveying a substance to the surface of a substrate, a means for creating a seal around a "spot deposition area" on the surface of the substrate, and a means for conveying unbound substance from the surface of the substrate. The microchannels may be of any length, and/or diameter. In one embodiment, the inner diameter of the conduit/channel is 100 µm, 90 µm, 80 µm, 70 µm, 60 µm, 50 µm, 40 µm, 30 µm, 20 µm, and/or 10 µm. Additionally, microchannels in the nanometer range are also known in the art and may be used in the present invention. In one embodiment, the plurality of microfluidic pathways of a spotter consists of a plurality of different inner diameters.

Figure 4:
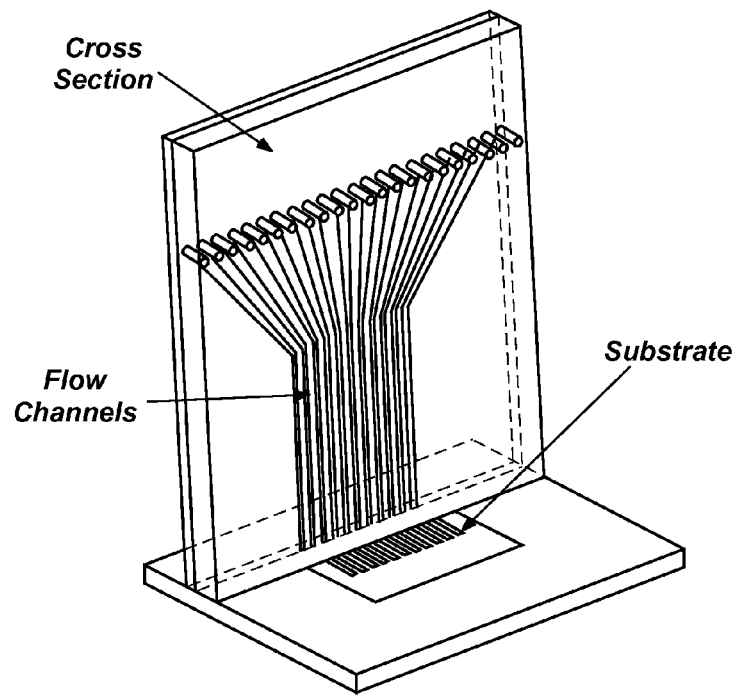
FIG. 4 is an illustration of a multi-orifice spotter.

FIG. 4 illustrates a multi-orifice spotter embodiment. Each pair of microchannels in this embodiment has an inlet and outlet separate from the inlets and outlets of the other microchannel. FIG. 4 discloses a row of the microchannel pairs, for example, as shown in FIGS. 1-3. As will be recognized in light of the present disclosure, the row of microchannel pairs illustrated in FIG. 4 may be configured as a single row or as multiple rows, likewise, the spacing between microchannel pairs in the same row or in different rows may be varied to produce a desired print head or spotting pattern. The overall size of the spotter may be adjusted to accommodate as many microchannels pairs as necessary.

Figure 5:
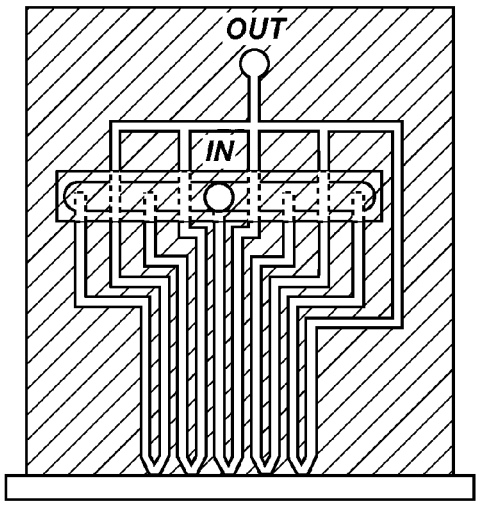
FIG. 5 is an illustration of a multi-orifice spotter.

FIG. 5 illustrates a multi-orifice spotter embodiment. In this embodiment, the inlets and outlets of each of the microchannel pairs are connected to a single inlet reservoir and a single outlet reservoir. FIG. 5 also illustrates two possible approaches to connecting the conduits to a reservoir, for example, the "outlet channels" are shown as an interconnected pathway, whereas, the "inlet channels" are connected via a manifold. In one embodiment, the inlets and/or outlets of a single row may be connected into a common row inlet and/or outlet, wherein a multi-row embodiment may have individual rows separately connected. For example, a spotter with a 1000 orifices, in a 100×10 configuration may have 10 row inlets and 10 row outlets, rather than 1000 inlets and 1000 outlets. This embodiment may be preferable when each row is to be spotted with a common probe, but a different probe is to be spotted on each row. Alternatively, all of the row outlets and row inlets may be connected to a single spotter inlet and spotter outlet. This embodiment may be useful when an entire array is to be made or treated with a single substance.

Figure 6:
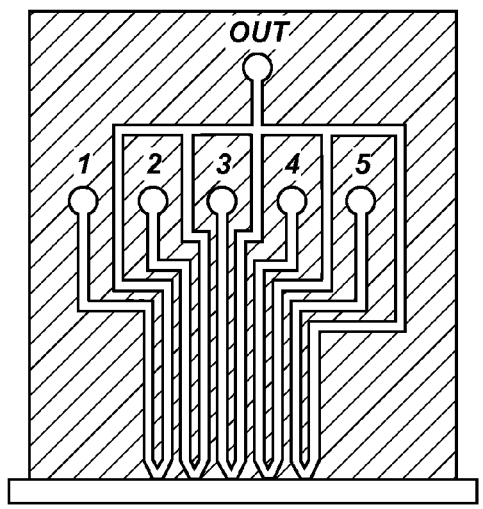
FIG. 6 is an illustration of a multi-orifice spotter.

FIG. 6 illustrates an embodiment where the inlet or outlets of a row are connected to one row outlet. One example of an intended use of this embodiment is when different substances are flowed through the individual inlets, but there is no desire to recycle the outflow, hence, a single outlet may be used.

In another embodiment, is for an outlet conduit connected to an adjoining inlet conduit to for a series of connected orifices. Using the spotter example with 1000 orifices, in a 100 by 10 configuration, in this embodiment, each row would have 100 orifices in a single fluid pathway and 10 fluid pathways. This embodiment is preferably used where an entire row is to be spotted with the same substance.

Figure 7:
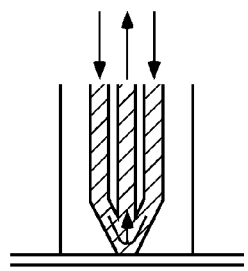
FIG. 7 is an illustration of a multiple inlet spotter as well as a cross-sectional slice of an annular embodiment of the spotter.

FIG. 7 illustrates two embodiments. The first illustrated embodiment comprises a fluid pathway having two inlet microchannels leading to a single spotted area and a single outlet microchannel leading away from the spotted area. This embodiment may be useful in the case of two different probes to be flowed over a spotted area without the need to change solutions in a reservoir or where it is desirable to have the separate fluid streams react with each other in close proximity to a substrate or an existing probe on a substrate. As will be recognized from this exemplary embodiment, more than two inlet microchannels may also be used. For example, 3, 4, 5, 6, 7, or 8 inlet microchannels may be used.

FIG. 7 may also be viewed as a cross-sectional slice of an annular embodiment. The annular embodiment may be created by placing a narrow microtubule within a larger microtubule or placing a narrow microtubule within a larger microchannel. Multiple microchannels may also be contained within a larger microchannel. For example, multiple inlet microchannels, for example, 2, 3, 4, 5, 6, 7, or 8 inlet microchannels, each carrying a different substance could be within a larger microchannel that serves as the outlet microchannel.

Additionally, the embodiments discussed in relation to FIG. 7 may be used to create a desired flow pattern across the spotted area. For example, the different inlet microchannels may each carry the same substance, but the multiple inlet microchannels may be configured to affect the flow profile over the substrate. When two or more inlet microchannels are flowing substances over the substrate at the same time, the substances collide directly over the substrate and the turbulence of this collision may be controlled to affect the binding of substances upon the substrate.

However, multiple inlet microchannels that fluidly connect to the same orifice may also be used to flow different substances at different times. Referring to FIG. 7, one substance may be flowed through the left inlet microchannel, across the substrate and out the outlet microchannel, followed by a second substance flowed through the right inlet microchannel, across the substrate, and out the outlet microchannel.

In another exemplary embodiment, multiple orifices each having multiple microchannels per orifice, for example, each microchannel labeled as A, B, and C, it may desirable to connect all of the A channels, and likewise for the B and C microchannels.

Any combination of the exemplary embodiments illustrated in FIG. 4-7 may be incorporated within a single spotter. For example, a spotter may contain a fluid pathways such as that disclosed in FIG. 4, other fluid pathways having inlets and outlets that are connected as discussed in relation to FIGS. 5 & 6, and yet other fluid pathways having multiple inlet microchannels such as that disclosed in FIG. 7, or any combination thereof.

The orifices in the spotter face may be arranged so that the spotted areas created on a microassay are in chessboard pattern. In other words, that the centers of each spotted area on the resulting surface form a square grid with the other centers. The orifices may also be arranged so that the spotted areas are in a honeycomb pattern so that the centers of each spotted area form equilateral triangles with the adjacent centers. Additionally, the orifices may be distributed within the spotter to produce a mixed field of a chessboard pattern and a honeycomb pattern.

Any number of orifices may be included within a row, and any number of rows within a spotter. A spotter preferably contains at least about 10, 50, 100, 400, 900, 1,600, 2,500, 10,000, 50,000, 100,000, 500,000, 800,000, 1,900,000, 3,000,000, 5,000,000, 7,000,000, 13,000,000, 29,000,000 orifices. The spotter also preferably contains at least about 10, 50, 83, 416, 500, 833, 1000, 4166, 5000, 8,333, 10,000, 20,000, 40,000, or 41,666 orifices per $cm^2$. For example, if the orifices are formed from 50 micron outer diameter microtubules packed in a chessboard pattern, then each square centimeter of the spotter face would contain 40,000 microtubules. The orifices can also be any diameter. The inner diameter of the orifices is generally less than 300 microns, and preferably 100 microns or less.

The microchannels have been illustrated in a vertical orientation such that the proximal ends of the microchannels rise vertically above the distal ends of the microchannels where the orifice is formed. For example, a spotter could be created where orifices and microchannel connections, such as those shown in FIGS. 8A-8C, are integrated vertically relative to the surface. However, the microchannels may have a wide variety of orientations including horizontal. As will be recognized in light of the illustrations herein, the fluid pathways may have bends, turns, or couplings from the orifice of the spotter to any fluid connections in the spotter. The terms fluid pathway and microchannel are intended to describe a path from the point of entry for a solution, e.g., a reservoir connection to the spotter, to the orifice, and away from the surface to be contacted by the orifice, e.g., a second reservoir. For example, FIG. 2 shows a single fluid pathway where syringe needles serve as the fluid connection means between the reservoirs (e.g., the syringe barrel) and the spotter. Still referring to FIG. 2, the term "inlet microchannel" includes the channel from the "fluid in" point to the orifice, and the term "outlet microchannel" includes the channel from the orifice to the "fluid out" point.

As will be apparent from the description herein, the conduits may be any length. A conduit may be 500 microns, 1 mm, 5 mm, 1 cm, 5 cm, 10 cm, 20 cm, or 100 cm or more in length. The ratios of conduit length to conduit inner diameter may be 5, 10, 15, 20, 100, 500, 1000, 10,000, or 30,000. All of the microchannels of a spotter do not have to be of uniform length.

A microchannel having a longer length, exposed to the same pressures as a shorter microchannel, will have a lower flow rate than the shorter microchannels. The lower flow rate results from the increased friction a substance experiences while flowing along the additional length of conduit. The flow rate may be calculated using a modified version of the Bernoulli equation.

Different flow rates for different fluid paths may be intentionally created, since the binding ability of probes to a substrate or surface is affected by the flow rate. Two factors should be considered when determining the appropriate flow rate. First, a probes residence time over a substrate is determined by the flow rate of the solution containing the probes. Some probes may require different residence times for optimal binding to a substrate. Therefore, the flow rate of the solution may be altered to increase the probability that a probe will or will not bind to a substrate. Second, as the flow rate increases the shear force across the substrate surface increases, which also affects the binding ability of probes to a substrate. If the flow rate is too non-specific binding and/or clump may occur. Clumping and/or non-specific binding may adversely affect the efficacy of the resulting array, for example, by unclumping of a probe at an undesirable time. Alternatively, if the flow rate is inappropriately high, in efficient binding of the probes may result (e.g., the probes may be effectively washed from the surface or may have insufficient residency in proximity to the surface for the desired binding). Therefore, the present invention provides a mechanism and means for controlling the flow rate of specific probes to provide for optimal binding for a probe in solution or suspension. It should be noted that as used herein a "solution" includes a suspension, however, for the purposes of illustrating the invention the term solution is used.

The effect of the flow rate was shown by creating an array of Protein A (Immunopure Protein A, Catalog No. 21181, Pierce Inc.) via a spotter with 8 orifices, comprised of 4 duplicate flow rates, having a flow rate of 20 µL/min, 16 µL/min, 13 µL/min, and 12 µL/min. The variations in flow rate were created by proportional changes in the lengths of the microchannels leading to and from each of the pairs of orifices. Analysis of the resulting binding, using surface plasmon resonance (SPR), showed that the first pair (20 µL/min) had low binding to a streptavidin-gold complex on the substrate. The fourth pair also had low binding to the substrate, but the second and third pairs had much better binding than both the first and third pairs, demonstrating an optimization of the flow rate.

Figure 16:
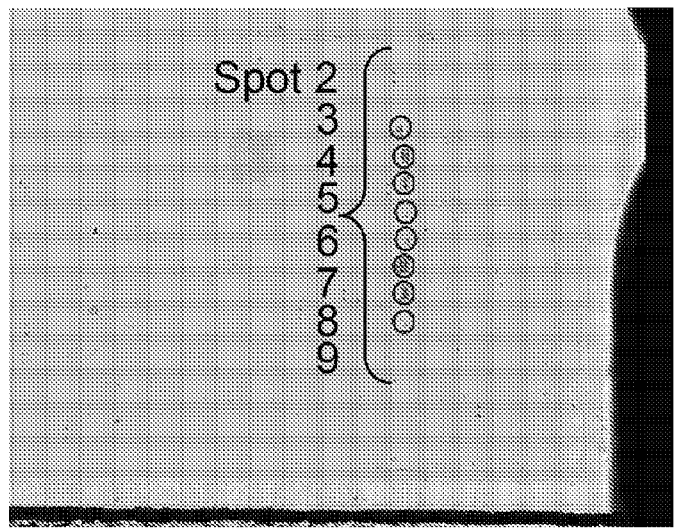
FIG. 16 illustrates an assay created by an inventive spotter.

FIG. 16 illustrates the array created by the above experiment. The replicates are mirrored from top to bottom, i.e. Spots 2 and 9, or 3 and 8, were generated at the same flow rate. Spots 3, 4, 7 and 8 demonstrate the highest level of binding (darker spots) as compared to the other spots, indicating that the flow rate required for optimal binding occurs between about 13 and about 16 µL/min.

This experiment also illustrates that a spotter with varying conduit lengths may be used to produce an optimal flow rate for each fluid pathway. Of course, it is also possible to alter the flow rate by other means, including increasing the pressure applied to the fluid or a combination of differing conduit length, diameter, and/or pressure. The flow rate may be calculated based upon the length/diameter of the conduit using a modified Bernoulli Equation. Optimization or determination of the appropriate flow rate may also be determined empirically, for example, by depositing a sample at one or more predetermined flow rates, testing the binding, and identifying the optimal flow rate.

The flow rate could also be adjusted to control deposition of different substances within a solution. For example, if a solution contains two different proteins, and the first protein has specific binding at a low flow rate, and the second protein has optimal binding at a high flow rate, then the binding of the substances may be controlled by varying the flow rate of the solution. The present invention also provides the ability to lay down a first substance, and then a layer another substance on the first substance, either by flowing two different solutions or by varying the flow rate of a single solution having both substances.

As will be recognized by a person of ordinary skill in the art, varying conduit length is just one means of varying the flow rate of substances in the spotter. Other means for varying the flow rate include varying the pressure with pumps, vacuums, or by moving the position of the reservoirs, changing the diameter of the microchannels, or any other suitable means.

The microchannels may be rectangular channels, circular (e.g., as shown in FIG. 1), triangular, or any other desired shape.

The figures illustrate spotter devices using microchannels and microtubules to carry substances to the spots/wells of an array. However, any conduit will suffice.

There are numerous other means for providing a fluid pathway to a specific spot on an array and flowing a substances over that spot. Flexible tubes with an orifice may also be used. Another option is rigid microtubules mated together in a "V-shape" with the orifice at the bottom of the "V." With microchannels, it is necessary that the microchannels be channeled in a structure, for example, the spotter body. Of course, tubes themselves may be bundled together to form the spotter body. Numerous means of connecting microtubules together are known in the art.

In another exemplary embodiment, a combination of microchannels and microtubules are utilized to form the spotter. For example, microchannels may be used to form structures such as those shown in FIG. 8, and then microtubules could be attached to the distal end of the microchannels. The microtubules could be arranged vertically, horizontally, or any angle necessary.

Substances may be moved through the spotter conduits either by pressure-flow, gravity-flow, electrokinetical means, air pressure, any other suitable means, or combinations thereof. Numerous ways for creating pressure-flow and gravity-flow are known, for example, pumps and vacuums. If the proximal end of an outlet conduit is lower than the proximal end of the corresponding inlet conduit a siphon may be established for flowing a substance through the spotter. Many of the substances that may be flowed through the conduits are charged, e.g., DNA having a negative charge, therefore, electrokinetic pumps may be used to move charged substances within the conduits. Air pressure may be used, for example, to push a plug of a viscous gel along the fluid pathway to propel a solution or a reservoir may be pressurized to propel the solution. Additionally, it may desirable to dope or coat the interior of the conduits to increase the negative charge of the conduits, which will reduce the friction between negatively-charged substances and the interior of the conduits.

1.2 Orifices

Numerous orifice designs are contemplated by the present invention. FIGS. 8A-8C illustrate just a few of the possible orifice structures. The invention simply requires that there be an orifice in a fluid pathway, adapted to deposit a substance on a surface. FIGS. 8A and 8B illustrate orifices that are approximately the same area as the microchannels. However, the cross-sectional area of the orifice may be larger than the cross-sectional area of the fluid pathway, as shown in FIGS. 8C and 9, or have a narrower cross-sectional area (not shown). The orifices are typically square, rectangular or circular; however, any geometric shape may be used.

The junction of the distal ends of the conduits that terminate near or at the orifices define what is referred to as a cavity. The cavities may have a wide variety of shapes and incorporate numerous structures. The cavities may be formed separately from the conduit or formed by the conduit, and may be designed with flow constriction and turbulence inducers to create different flow patterns and shear forces across a spotted area on a substrate. FIG. 6 illustrates angled one-direction flow over the substrate surface. FIG. 7 illustrates how two inlet microchannels can be designed to intersect over a single spot. The intersecting flow pattern could allow for confined reactions to occur directly over a spotted area. Additionally, if only one substance is flowed at a time, the FIG. 7 embodiment may be used for sequential processing of the spot with different substances. Of course, more than two inlet microchannels may be connected to a cavity. Furthermore, two conduits do not have to physically connect to form a conduit. For example, FIG. 7 can also be viewed as a cross-sectional slice of one microtubule within a larger microtubule, where the first and second conduit do not have to contact one another to create the cavity.

FIG. 8A illustrates a cavity where the inlet microchannel is at an angle to the substrate and a mixing vane is included within the cavity. FIG. 8B illustrates a ninety degree turn in the inlet microchannel to allow for the lateral infusion of substances over a substrate and to increase turbulence, and hence mixing. FIG. 8C illustrates a cavity that allows for lateral injection, flow across the substrate surface and then vertical venting of the substance. Additionally, cavities such as FIG. 8C may be used to modify the substrate surface. Structures may be micromolded, via the spotter, upon the substrate such as optical guidance structures for communication devices or microscaffolds for cell cultures.

Figure 15:
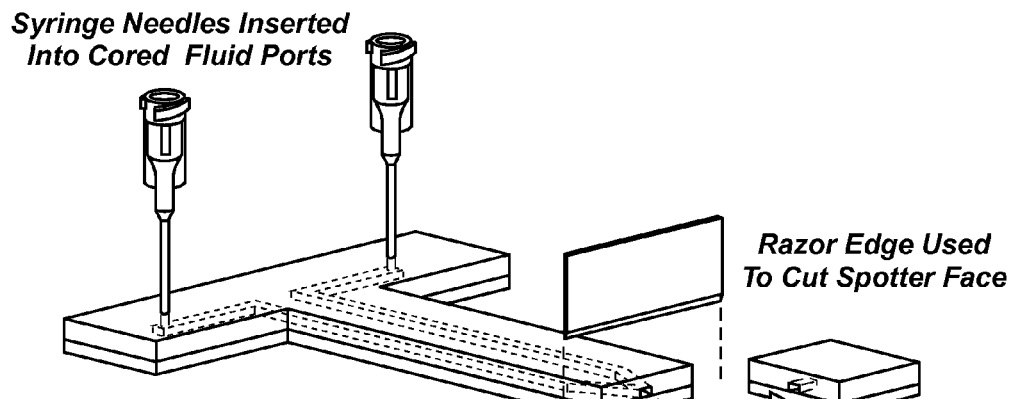
FIG. 15 illustrates a method of spotter face cutting.

The spotter face refers to the spotter surface that mates with a substrate upon which a substance is to be flowed, such as a microarray substrate. FIG. 15 illustrates a spotter face on a single orifice embodiment. FIG. 15 is illustrating a step in one method of fabricating a spotter, where the spotter face is the surface on the spotter in FIG. 15 created after the end material is removed. As can be seen in FIG. 4, the spotter face may be a flat surface regardless of the number of orifices included within the spotter. Viewing the spotter face in the horizontal plane, when it is desired that the spotter face be a flat surface it is preferable that the orifices deviate from each other less than 1 mm in the vertical plane, even more preferable less than 100 microns, even more preferable less than 50 microns, even more preferable less than 20 micron, and even more preferable less than 5 microns.

However, the spotter face does not have to be a flat surface. The spotter face may be just the orifices of the distal ends of a bundle of microtubules. In this embodiment, if the orifices are circular, the spotter face would be a collection of rings. In a bundle of microtubules, gaps, rather than a solid surface, may be present between the outer edges of the orifices. These gaps may also be filled in, if desired, by methods known in the art. For example, in the microtubule embodiment, the microtubules may be held together by an epoxy used to fill in the gaps between the channels. The cured epoxy and channels may then be cut and/or polished to form a smooth surface.

Additionally, the spotter face can be designed to correspond to any structure on a substrate. For example, if a substrate has ridges, the spotter face may be modified to have valleys that mate with the substrate ridges or visa versa. The spotter face may also be made rigid or of sufficient flexibility to conform to a substrate surface.

The spotter face may be any size or geometry. The spotter face may be designed to cover a 76 cm×26 cm microscope slide, or even a 25 mm, 50.8 mm, 76.2 mm, 100 mm, 125 mm, 150 mm, 200 mm, or 300 mm wafer. There elegant simplicity of the present invention allows for a spotter face of nearly any size or geometry.

1.3 Accessory Structures

Thermoregulatory and/or gas exchange elements, which may comprise microchannels that do not terminate at an orifice in the spotter face, meaning there is no direct contact with a spotted area on a substrate, may also be used in the spotter. FIG. 9 illustrates an additional microchannel incorporated within the body of a spotter that is in close proximity to an orifice. The additional microchannel in FIG. 9 is used to control the amount of a gas near the spotted area, for example, controlling the concentration of $CO_2$ when spotting or assaying cells. The additional microchannel in this embodiment should be close enough to the spotted area to allow gas to diffuse through the walls of the spotter material, but far enough away to maintain the structural integrity of the spotter. FIG. 9 discloses the additional microchannel as narrower than the microchannels that lead to the spotted area, however, the size and structure of the element will depend upon the application. FIG. 9 shows one additional microchannel per spotted area; however, the spotter could be designed such that one additional microchannel controlled the gas diffusion for several spotted areas. For example, one additional microchannel could be designed to be equal distance from either 2, 3, or 4 orifices. FIG. 9 shows an additional microchannel to one side of an orifice; however, the additional microchannel may be designed to completely encircle the orifice.

Other additional microchannels or thermoregulatory elements may be incorporated within the spotter for temperature control. Additional microchannels or thermoregulatory elements may be used for heat exchange in the spotter, for example, a electrically resistive wire inserted into the spotter to heat the spotter face or a fluid pathway. The temperature controlling microchannels or thermoregulatory elements may be placed as needed within the spotter. The temperature controlling microchannels or thermoregulatory elements may be designed to spiral just near the orifices, along the length of the inlet conduit, or around the entire spotter itself.

Other structures may also be incorporated within the spotter itself. A few examples are heating coils and pumps. The heating coils may be incorporated during fabrication with a preformed coil or by forming a line of sufficiently electrically resistive metal alloy by semiconductor fabrication techniques. FIG. 10 discloses one pump embodiment. In that embodiment a chamber with a flexible membrane is created within the spotter and coupled to an outlet microchannel. Pressure can be applied and released repeatedly to the flexible membrane to allow a substance to be oscillated back-and-forth through the conduits and over a spotted area.

Additionally, the embodiment shown in FIG. 10 may be modified to flow fresh substance in one direction through the conduits. Referring again to FIG. 10, if an outlet microchannel that exited the spotter was added to the flexible cavity and two one-way valves, such as ball float valves, are added at some point before and after the flexible cavity, then a one-way pump would be created. In this embodiment in may be necessary to incorporate a spring mechanism within the cavity; however, the flexible membrane may be sufficiently resilient to serve as the spring. Additionally, the flexible membrane may be replaced with a piston or any other type of pump device. A pump incorporated within the spotter may or may not need additional valving.

Any number of devices may be attached to the spotter. A few examples are pumps, blowers, vacuums, fluid lines, heating/cooling jackets, mounting hardware, and reservoirs such as beakers or microtiter plates. All of the inlet microchannels may feed from and all of the outlet microchannels may return to the same reservoir. Or each inlet microchannel may feed from a unique reservoir where only a single outlet microchannel returns to that reservoir, or there may be no return flow to that reservoir from an outlet microchannel. Any number of variations are possible and are within the scope of the invention.

1.4 Robotic Systems

The spotter of the present invention may be incorporated within a robotic spotting system. It may be simplest to integrate the spotter into a non-contact arrayer as the fluid dispensing hardware and flow control, valving, etc. is already integrated into the arrayer. However, any type of robotic arm and system can be made to work and so the spotter could be integrated into the system of a contact arrayer, such as a pin-spotter, as well. A few examples of non-contact arrayers are the BioJet Quanti™ by BioDot and the synQUAD™ by Cartesian Dispensing Systems™. A few examples of contact arrayers are SpotBot® by Telechem International, MicroGrid by Genomic Solutions®, QArray® by Genetix, and 3XVP by Radius Biosciences.

Robotic systems incorporating the inventive spotter may have the benefit of not requiring the robotic arm to rotate from side-to-side. The robot would only have to move the spotter up and down and potential forward and reverse. Pin spotters, for example, must rotate from side-to-side in order to re-dip the pins.

2.0 Uses 2.1 Microassays

The spotter of the invention provides each spot with its own individually addressed microfluidic channels, and a large-number spot arrays can be addressed in parallel. Constant substance flow can be maintained for an extended period of time to allow spotted areas to build a high-density spot. This technique allows for much higher signals to be generated than when standard concentrations are used with traditional spotters. The higher signals increase the signal-to-noise ratio, and thereby allow better data to be collected. Lower concentration solutions may also be used with the spotter and still yield satisfactory results, which would result in a cost savings. A few examples of assays that may be conducted on an array are fluorescence spectroscopy, chemiluminescence detection, color-staining, other optically-based microarray sensing technologies, or radiometrics.

The spotter may be used to produce two-dimensional arrays. The spotter thus has the potential to fabricate microarrays with an unlimited number of defined spots, with each spot individually tailored to a specific deposition density. The spotter may also sequentially chemically process individual spots, either through the use of the same spotter or through multiple spotters. The spotter may be used to perform layer-by-layer self-assembly (LBL) to build up spot concentration. Multiple layering and washings on the spotted area may be performed simply by changing the substance that is flowed over the spot. Additionally, the surface of the substrate may be modified by flowing the appropriate material through the spotter. Surface modification of the internal walls of a spotter microchannel may be performed using solutions, such as BSA (bovine serum albumin) to reduce binding of a substance. In an exemplary embodiment, the spotter is a disposable spotter, thereby eliminating contamination issues.

Preferably, the spotter allows for fabrication of spots with low cross-talk and low background noise, due to the sealing of the surface of the microassay with the spotter orifices.

In an exemplary embodiment, a microassay having relatively small spots is created with a spotter having relatively small orifices, and a second spotter with larger orifices may be positioned over the same microarray. This may be useful for drug interaction testing where different probes, such as proteins, are spotted onto an array, and then a drug or chemical compound is flowed over the proteins on the array.

A microarray may contain any number of probes, and preferably the number of probes in the microassay is at least about 500, 1000, 5,000, 10,000, 50,000, 100,000, 500,000, 800,000, 1,900,000, 3,000,000, 5,000,000, 7,000,000, 13,000,000, or 29,000,000. Substances, such as probes, may be affixed or bound to the microassay substrate in a number of ways: covalently; non-covalently through e.g. ionic, polar, or Van der Waals forces or conformational interaction of binding moities such as biotin-avidin or biotin-streptavidin; attaching the substances or probes to beads (magnetic or non-magnetic); or any other method. If the substances or probes are first attached to magnetic beads, then magnetic attraction may be used to affix the beads to the microassay substrate. Additionally, when using magnetic beads, magnetic fields may be used to control the flow of the probes within the conduits of the spotter.

U.S. Pat. No. 6,594,432 to Chen et al. ("'432 patent"), entitled "Microarray Fabrication Techniques and Apparatus," incorporated by reference, discloses the use of capillaries, such as silica tubes, to spot probes onto a substrate. The describes substrates with a light sensitive coating that may be hydrophobic but turn hydrophilic upon exposure to light of the appropriate wavelength. Using tubes capable of conducting light and a substrate with a light sensitive coating that is initially hydrophobic, light may be transmitted through the light-conductive tubes prior to spotting the substrate. This creates regions on the substrate that are now hydrophilic while the substrate surface surrounding the regions are still hydrophobic. Probes in a polar solvent, such as water, are then spotted onto the substrate. The regions of hydrophobic surface may then be kept from spreading out over the substrate surface.

The present invention may also utilize light-conductive fluid pathway structures if desirable. Numerous methods for creating light-conductive microtubules and microchannels are known. For example, silica tubes may be coated with a polymer that has a slightly lower refractive index than the refractive index of silica to create light-conductive microtubules. Alternatively, the outer surface of the tubes may be doped with fluoride during fabrication of the tubes, which will result in an outer layer that has a lower refractive index than the rest of the tube. Finally, fluid in a silica tube, having a slightly higher refractive index than the fluid, may be used to transmit light. For example, during fabrication microchannels may be layered with a suitable polymer and then layered again with silica. Other materials than silica are also capable of conducting light and amenable to semiconductor fabrication techniques. Therefore, the microchannel may be layered with any suitable light conductive material.

2.2 Cell Cultures

Referring to FIG. 9, the spotter can be used to deposit live cells, either singly, in groups, or in a matrix such as a hydrogel on the substrate, thus creating arrays of cells suitable for high-throughput assays, such as drug screening or drug discovery. If each spot area is individually addressed, then different types of cells can be deposited at each spot and/or each cell spot addressed with different chemicals. This allows for more information to be obtained from the microarray than a uniform or semi-uniform cell array. Additionally, the cells can be sustained while the orifice is sealed against the substrate, by using the conduits to feed the cells. Dissolved gas in the media surrounding the cells may be controlled by integrating additional conduits adjacent to the spotter orifices. This may be particularly beneficial when the spotter is composed of highly gas permeable materials such as PDMS [2]. Cells could be optically monitored from below the culture, or via waveguides/fibers integrated into the spotter itself.

Figure 11:
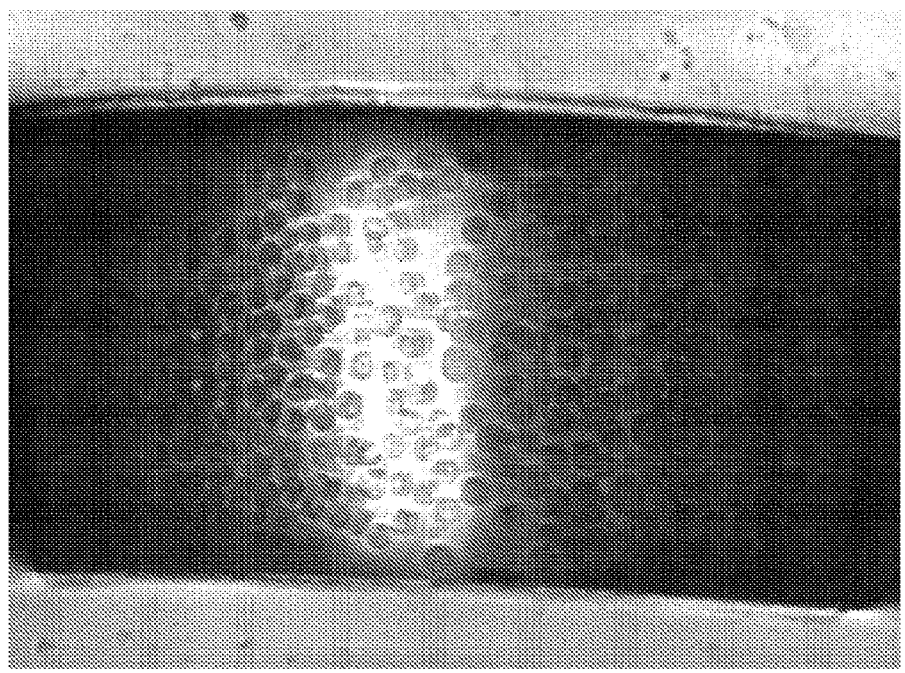
FIG. 11 illustrates a cell spot create with a spotter.

FIG. 11 is a picture of a cell culture spot created with the inventive spotter. Chinese hamster ovarian cells (CHO) cells were deposited on a polystyrene substrate in 500 µm×750 µm spots, using a plug of solution. The cells in solution were flowed to the orifices, the flow was stopped to allow the cells to adhere to the substrate, and then the excess unbound cells were washed off by flowing cell growth media over the spots. All these operations were carried out while the spotter was pressed against the substrate. To prevent the cells from adhering to the inside surface of the spotter microchannels, a 0.63 mol/L solution of the pluronic F108 Prill Surfactant (BASF) was flowed into the microchannels, and allowed to incubate overnight.

Prior to spotting the cells, cell culture medium was flowed through the spotter over the substrate at 6 mL/hr for 4 minutes. 300 µL of CHO cells in a $655\times10^4$ cells/mL suspension were prepared and pumped down to the spots with a syringe pump at a flowrate of 3 mL/hr for 8 minutes. The low flowrate was used to prevent damage to the cells by fluidic shear forces. The flow was then stopped for 20 minutes to allow the cells to adhere to the substrate. Cell culture media was then flowed through the spotter at 3 mL/hr for 8 minutes to wash off the excess cells. To prevent the cells from desiccating, the spotter was left interfaced to the surface while the cells were imaged on an inverted microscope. FIG. 11 is an image of the cells deposited on the substrate.

Numerous cells and substrate combination are possible. If necessary, warming devices such as heating coils may be incorporated within the spotter.

2.3 Biosensors

The spotter and system may be used in fabricating biosensors where the substrate is a transducer and the biolayer to be bonded to the transducer is transported to the transducer via the spotter. Additionally, the system and spotter may be used to administer biomolecules or chemicals to test existing biosensors.

Biosensors may be viewed as enhanced microassay. The surface of the biosensor is an array of probes. When a target compound reacts with a probe at a particular spot on the biosensor surface, an electrical signal is generated that is identified with the particular spot on the surface. The probes at the particular spots are often in a fluid solvent. The reaction of the probe and the target compound may be detected by a photodetector which records a change in intensity of reflected light after the reaction occurs. Another detection option is to monitor the electrical properties of the fluid solvent surrounding the probe for changes.

The spotter may be used to more quickly and inexpensively create and operate biosensors. One example of how this may be accomplished will be described in relation to U.S. Pat. No. 6,699,719 to Yamazaki et al. ("'719 patent"), entitled "Biosensor Arrays and Methods." The '719 patent discloses a biosensor where the individual array spots have a fluid bi-layer membrane with surface properties similar to those of living cells. This could be beneficial where bi-layer membranes can be constructed similar to different human cells, such as T-cells, muscle cells, nerve cells, sperm cells, and etc. The '719 patent discloses including specific receptors within the bi-layer membranes, and then exposing the receptors to a wide range of ligands to determine which ligands will bind with the receptors. The '719 patent gives the example where acetylcholine receptors (ACHR) are included in at least some of the bilayer membranes and then the biosensor may be flooded with a solution of unknown composition to detect the presence of acetylcholine (ACh). Similarly, the AChRs may be used to test for compatibility of ACh-like compounds. Such a process would be useful for drug discovery.

The '719 patent discloses the following method for building a biosensor. First, a substrate is modified to have raised or depressed structures which form chambers. The chambers need to be of a material that is "bilayer-compatible" and the chambers need to separated from each other by "bilayer barriers" that are not "bilayer-compatible." The bilayer membranes are formed from liposome containing the desired receptors. The liposome suspensions must be applied to the substrate in a humidified chamber to avoid evaporation fluid loss. Liposome suspensions are applied as micro-droplets to the chambers on the substrate. Two options mentioned in the patent for micro-droplet administering are the use of modified ink-jet printing devices and micropipettes. The entire surface of the substrate is then flooded with an aqueous solution until the substrate chambers are filled but not overflowing. The chambers are sprayed with a mist of the same aqueous solution until the liposome micro-droplet spread out into a film. Next, additional aqueous solution is added to the substrate. Sufficient forces are present to keep the liposome, which is the bilayer membrane mentioned previously, within the substrate chambers. The biosensor is now ready for use.

The inventive spotter would greatly aid the formation of biosensors similar to that disclosed in the '719 patent. First, the spotter orifice creates a seal when placed against a substrate. Therefore, a flat substrate of entirely "bilayer-compatible" material may be used, such as silica. The "chambers" are created upon the surface by the spotter orifice and the walls of the conduits. The use of a flat substrate greatly simplifies the manufacturing process. Second, it is not necessary to flood the entire substrate with an aqueous solution. The spotter conduits can deliver the appropriate amount of aqueous solution. Third, the same spotter conduits that delivered the aqueous solution can deliver the micro-droplet liposome solution, or alternatively, a separate conduit can deliver the micro-droplets. The spotter has the advantage of not needing a separate humidified chamber that must enclose the micro-droplet administering apparatus. The proximal ends of the spotter conduits and any fluid connections to reservoirs can easily be sealed, turning the conduits of the spotter itself into a humidified chamber. Additionally, there would not be any alignment issues inherent in trying to line up ink-jets, micropipettes, pins, and etc. with the substrate "chambers." No longer requiring a humidified chamber and the avoidance of alignments is a further great boon. Fourth, spraying the liposome micro-droplets could also be accomplished within the chambers created by the spotter orifices and conduits. Conduits can be incorporated within the spotter that included a nozzle aimed at the orifice. The aqueous solution could be flowed through the nozzle to mist the micro-droplets. Fifth, the final amount of aqueous solution could be added via the spotter conduits.

The biosensor is now ready to have target compounds, such as ligands delivered via the spotter conduit. Exact compositions or unknown mixtures may be flowed to each "chamber." Use of the spotter would reduce the risk of contamination, because the biosensor "chambers" are never exposed to an environment outside of the spotter where dust or other contaminants are possible. Of course, any necessary incubation time between biosensor formation steps may be accomplished with the spotter as well. Furthermore, use of the spotter may facilitate combining the second and third steps. The spotter alleviates the need to flood the entire substrate with the aqueous solution. Therefore, it may be possible to flow the liposome micro-droplets with the aqueous solution to the substrate in one step rather than in two. Also, if necessary, the distal ends of the spotter conduits could be doped to increase the "bilayer-compatibility" of the conduits. This may be beneficial so that after the fifth step when the final amount of aqueous solution is added to the "chamber" the liposome does not rise to the surface of the aqueous solution, but instead remains submerged at the level of the doped region of the spotter conduits.

2.4 Biochips

The spotter may be used to simplify biochips. Biochips are attempts to create "labs on a chip" and are also known as micro total analysis systems (μTAS) [1]. The XEOTRON XEOCHIP® is one example of a biochip for DNA, also known as a DNAchip [4]. The XEOCHIP® may be used to build compounds such as DNA and RNA one base at a time. For example, an array was created on a XEOCHIP® with 254 genes with 30 replicates. The XEOCHIP® substrate uses microcanals to feed bases to individual chambers. The same base is flowed to all of the individual chambers at the same time. However, the base is only binds to the growing DNA or RNA chain if the chamber has been irradiated. Therefore, even though different oligonucleotides are being grown, all of the chambers may be fed the same base, guanine for example, but the guanine would only bind to the growing oligonucleotides in chamber that had been irradiated. This is because a photo-generated acid (PGA) is formed in the chambers that are irradiated. The inventive spotter could be used to simplify operation of the XEOCHIP®.

One possible simplification resulting from the use of the inventive spotter is the XEOCHIP® would no longer need to irradiate the chambers. The XEOCHIP® chambers occupy an area approximately that of a dime. That necessitates a precision micro-mirror system for properly irradiating only specific chambers. The spotter face of the inventive spotter could be modified so that the individual orifices of the spotter seal around the individual chambers of the XEOCHIP®. In this embodiment, instead of irradiating a chamber to form a PGA, a conventional DMT-protected phosphoramidite nucleoside with an appropriate acid could be flowed to only the chambers to be modified. However, that would result in some of the chambers not being fed a base. Another option with the spotter is to feed each chamber the appropriate base. Therefore, there is no time where an oligonucleotide is not growing, unless of course it is finished. In that embodiment, not only would there not be any need for mirrors, but the oligonucleotides may be grown quicker because there is no time where one chamber is being fed a base, but other chambers are not.

Additionally, once the oligonucleotides are grown, any desired target compounds may be flowed over the oligonucleotides via the spotter. Therefore, replicates of the same oligonucleotide could be fed different target compounds at the same time. Or, all of the oligonucleotides could be fed the same target compounds. The spotter could be used for growing the oligonucleotides, but not for subsequent testing. Or, the spotter could be used for both growing and testing of the oligonucleotides.

The inventive spotter may also be used to even further simplify growing of nucleotides. The XEOCHIP® requires the formation of a complex substrate with microcanals and chambers. The inventive spotter could also be used to grow oligonucleotides in the manner described above, but on a less complex substrate, such as a glass slide. The functions provided by the microcanals and chambers could be accomplished with the inventive spotter.

2.5 Other Substrates

The substrate may be formed of any material on which probes may bind. Porous or nonporous substrates may be used. Likewise, flexible and rigid substrates may also be used. Preferred substrate materials are silica, glass, metals, plastics, and polymers.

For immobilizing polynucleotides and polypeptides, glass is a preferred material because polynucleotides and polypeptides can be covalently attached to a treated glass surface and glass gives out minimal fluorescent noise signal. The glass may be layered on another material, or it may be core or base material, or both. Another example of a substrate includes a plastic or polymer tape as a base substrate, with a coating of silica. Additionally, a further layer of metallic material may be added, either on the opposite side of the tape from the silica layer, or sandwiched between the silica layer and the polymer or plastic.

The spotter conduits and orifices could also be designed for molding structures onto the substrate, such as with the orifice and microchannels shown in FIG. 8C.

3.0 Deposition Density Testing

Figure 12:
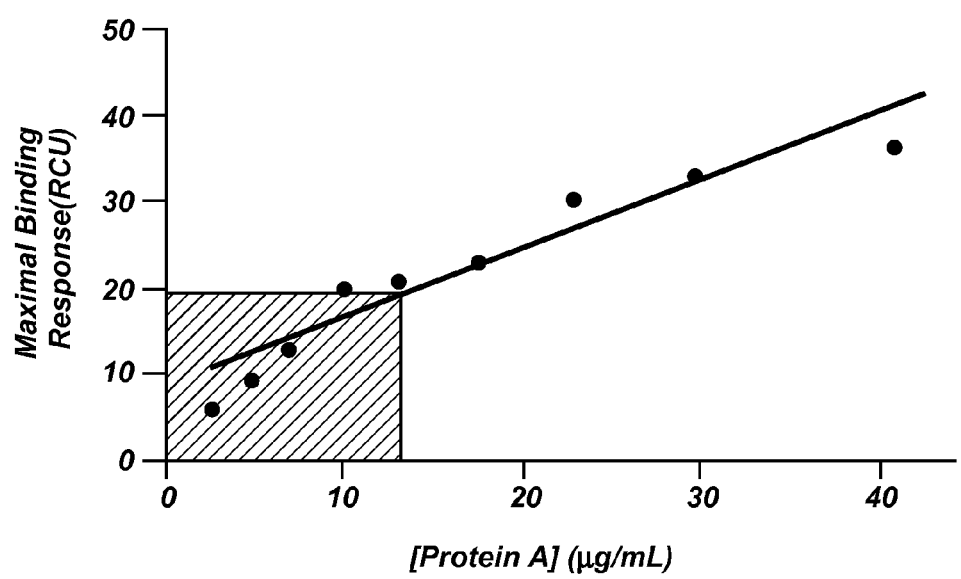
FIG. 12 is a graph of deposition density with an inventive spotter compared against a pin-spotter.

A first test was performed with a biotinylated protein that was deposited on a streptavidin/gold-coated substrate. Adsorption density of the protein was measured by surface plasmon resonance (SPR), and compared to a varying solution concentration curve generated with a Genetix QArray Mini pin spotter. Results, illustrated in FIG. 12, show a 0.15 μg/mL solution cycled through the spotter achieved the same results as 13 μg/mL pin-spotted solution, an 86-fold (8500%) increase. The procedures followed during these tests are detailed below.

Protein A (Immunopure Protein A, Catalog No. 21181, Pierce Inc.) was biotinylated with Biotin (EZ-Link Sulfo-NHS-Biotin, Catalog No. 21217, Pierce Inc.) to provide specific adhesion to a surface plasmon resonance (SPR) streptavidin gold chip (8500 streptavidin affinity chip, Part No. 4346388, AB). The protein solution was diluted to a concentration of 0.15 μg/mL in 0.1×PBS buffer (0.19 mM $NaH_2PO_4$, 0.81 mM $Na_2HPO_4$, pH 7.4 and 15 mM NaCl) and supplemented with 100 μg/mL BSA to prevent non-specific adhesion. To recirculate the solution over the chip surface, 200 μL of protein A solution was loaded into a Phynexus MicroExtractor 100 syringe pump and flowed continuously back and forth through the spotter at 75 μL/min for 1 hour. A wash step was then performed using 800 μL of 0.1×PBS with 100 μg/mL BSA. At the end, the sample was removed from the surface by withdrawing air through the assembly, and the chip washed with water. To compare the results of the continuous-flow immobilization, Protein A was also immobilized on the same chip using solid-pin spotting. Samples at the same concentration (0.15 μg/mL) as the ones used for the continuous-flow delivery test were spotted across the chip. Binding to the two sets of spots allowed a comparison of the sensitivities of the two immobilization methods. Solid-pin spotting was carried out using a Genetix QArray Mini spotter. A series of increasing protein concentrations were deposited using the pin spotter to create a calibration curve of SPR response to deposited Protein A concentrations. This curve was used to calculate an equivalent concentration of the spotter, to determine the factor increase in deposition density.

Figure 17:
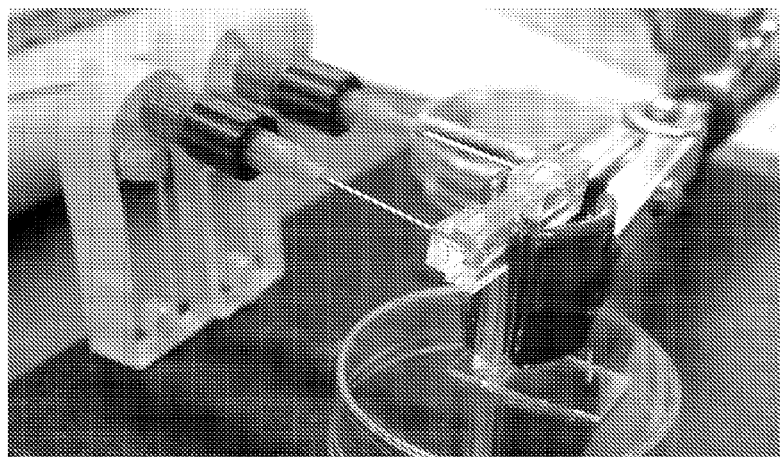
FIG. 17 is an illustration of a single orifice spotter performing deposition of dye solution on a glass slide.
Figure 18:
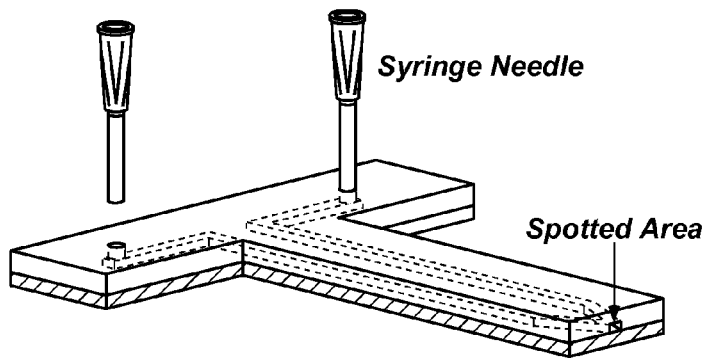
FIG. 18 is an isometric diagram of one example of a spotter, showing the orifice.
Figure 19:
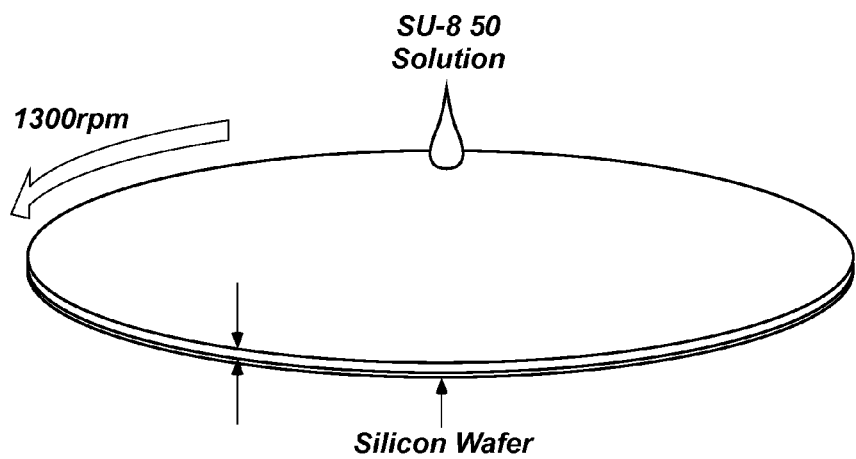
Figure 20:
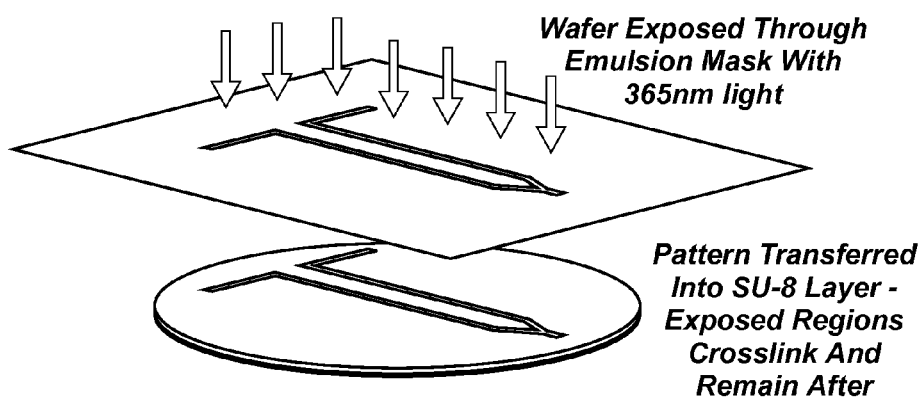

A second test was conducted with a macroscale single-orifice spotter manufactured by casting PDMS channels around a copper wire mold. The spot area was defined by a inserting the end of the mold wires into a 2 mm by 2 mm cube of PDMS, and the larger-sized spot produced was compatible with available fluorescence test apparatus. See FIGS. 2, 17, & 18. A fluorescent dye solution at 2 μg/L was recirculated for 60 minutes over a glass slide at 2 mL/hr to allow deposition to occur from the total 2 mL of solution. To simulate previous techniques, 3 μL of the same solution was dropped onto a glass slide and dried to form a spot of the same area as the spotter.

Figure 13:
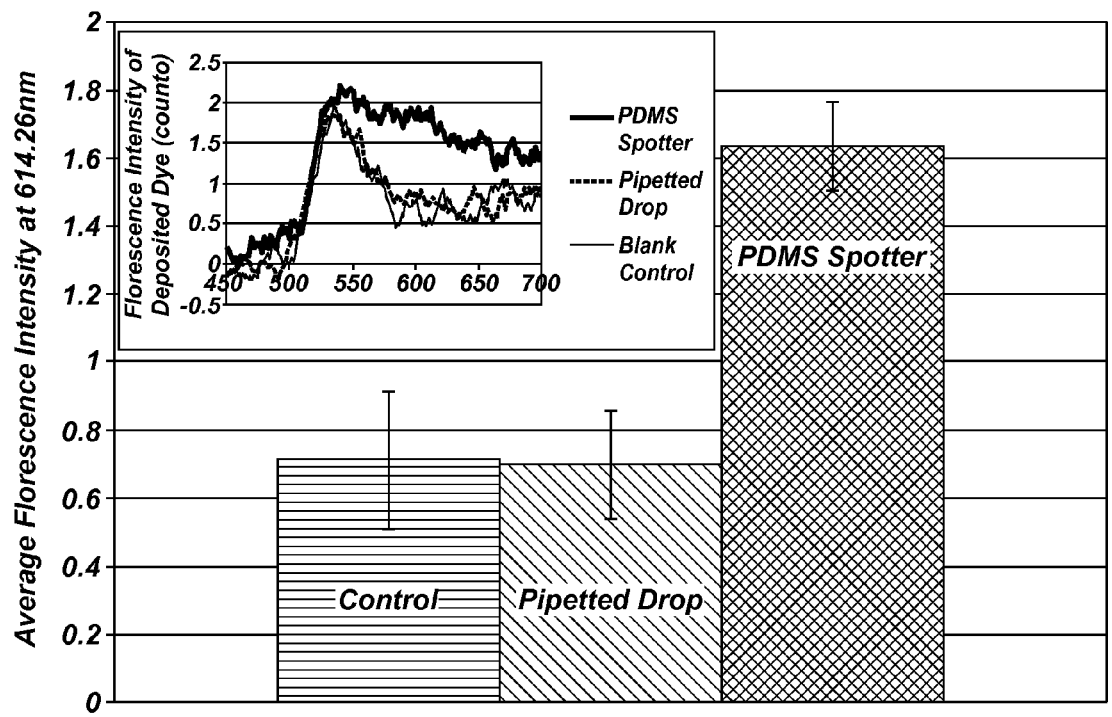
FIG. 13 is two graphs comparing the density of dye deposited with a spotter and dye deposited with a pipette.
Figure 14:
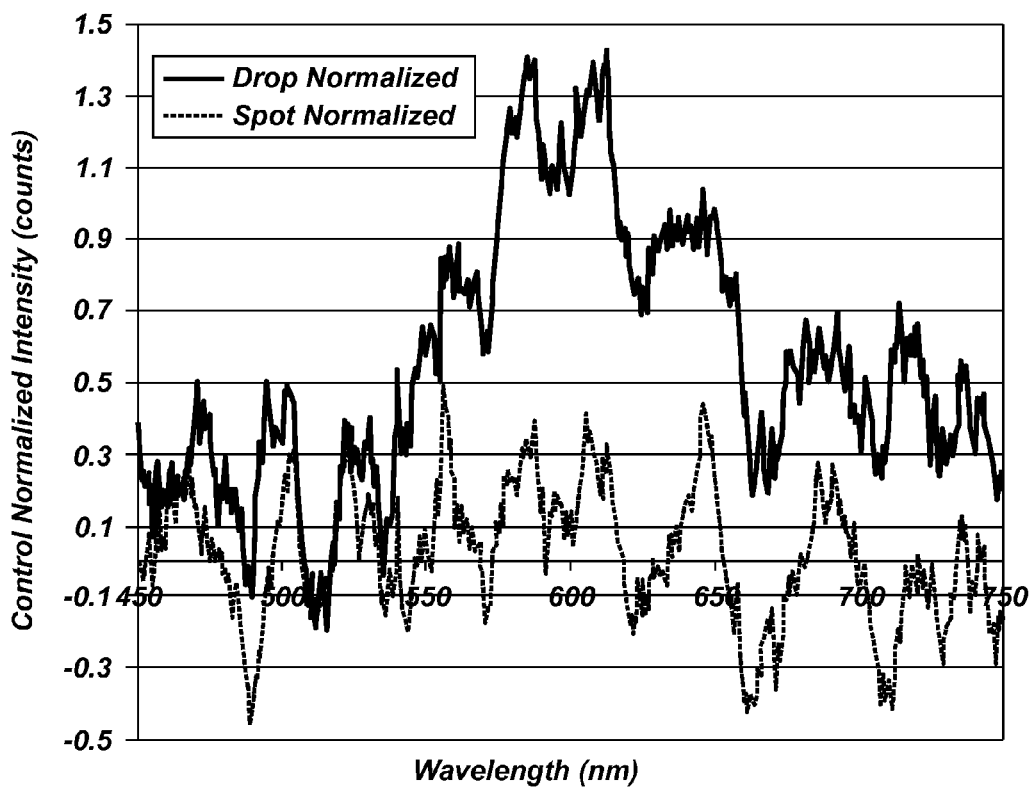
FIG. 14 is a normalized version of the inset graph in FIG. 13.

Comparison of the macroscale spotter system with existing deposition techniques yielded an approximately 5-fold increase in deposition density by the spotter, as shown in FIG. 13, as compared to a typical pin-spotter system. The error bars on the bar graph of FIG. 13 show one standard deviation for the data set. The inset graph on FIG. 13 shows the spectrograph for each test sample. The most important data in the inset is at 614 nm (the center of the fluorescence output). The peak that shows up in all of them is leftover that did not get filtered from the excitation peak. FIG. 14 is a normalized version of the insert graph of FIG. 13.

4.0 Fabrication

The spotter can be fabricated out of any material suitable for the method of fabrication that is compatible with the substances to be flowed through the spotter, such as silicon; silica; polydimethylsiloxane (PDMS); gallium arsenide; glass; ceramics; quartz; polymers such as neoprene, Teflon™, polyethylene elastomers, polybutadiene/SBR, nitrites, nylon; metals, any other material compatible with the a substance to be flowed through the spotter, and combinations thereof. It may be desirable to build the spotter out of material for which the substances to flowed have a low affinity for in order to reduce binding of the substance within the spotter microchannels. Additionally, the inner diameter of the conduits may be coated with suitable material to reduce the affinity between the substances being flowed and the conduits themselves.

The inventive spotter may be fabricated in numerous ways. A spotter may be fabricated by cleaning a wafer of suitable material, priming the wafer if necessary, adding material to the wafer via casting, molding, oxidation, deposition, or any other suitable method, subtracting material via machining, grinding, or etching or some other suitable method. Additional wafers may be bonded to the modified wafer. Additional material can be added or subtracted as necessary, or a combination of additional wafers and materials may be added as necessary to fabricate the spotter. Additionally, the above steps can be performed in any order necessary.

Additional fabrication methods are also possible. For example, rather than using semiconductor fabrication methods, a mold with stainless steel micro wires could be used. After an appropriate material has set, the microwires could be removed with the resulting voids forming microchannels.

Or a mold could be used to form the spotter face, and then microtubules could be mated to the back side of the molded spotter face. This might work well if the microtubules are inserted prior to curing the substance used to make the spotter face.

Additionally, the spotter may be fabricated almost entirely from microtubules. There are a wide variety of semiconductor fabrication techniques known in the art that may be used, not only with silica, but with other tube materials as well, to create, modify, and join the microtubules of the present invention. One technique for etching silica is that the portions of the silica tubes doped with Ge etch much quicker than the undoped regions. Therefore, tubes doped in the appropriate regions may be etched, and joined, if necessary, in a desired manner. Microtubules in the annular embodiment may not require etching at all, instead narrow microtubules are secured inside of larger microtubules.

Discussed below are a few fabrication examples using standard semiconductor fabrication techniques.

4.1 EXAMPLE I 4.1.1 Overview

Example I was followed to form a 4-orifice spotter. The fabrication process followed can be subdivided into five main steps: SU-8 mold fabrication and preparation, PDMS casting and curing; fluidic port coring; channel sealing with PDMS slab; spotter face cutting with razor edge. The entire fabrication process of this embodiment, including the SU-8 mold formation, took approximately 10 hours to complete.

A linear array of four 100 μm-sized channels was fabricated by casting the PDMS channels from a SU-8 mold that had been patterned lithographically [3]. Once the microchannels had been released from the mold, they were sealed closed with a slab of PDMS using an oxygen plasma. Packaging was achieved by coring a port through the microchannel substrate with a modified 20-gauge syringe needle and inserting an unmodified needle into the cored hole. The microchannels of which were arranged in pairs to each of the orifices, with each pair intersecting at a specific point. Each spot area was defined by cleaving the PDMS through the microchannel pair intersections to create an orifice on the cleaved face that is connected to a pair of microchannels. Since all the intersections were arranged in a line, a single cut was used to open all of the spots to one cleaved face, producing a linear array. The cleaved spotter face can then be pressed against a deposition substrate, and the cross-section of the orifices on the cleaved face will define the spot deposition areas. A more detailed description follows herein.

4.1.2 SU-8 Mold Fabrication and Preparation

The SU-8 mold was photolithographically constructed. An emulsion mask was fabricated prior to the mold using a high resolution printer (Lithopointe) and used as-is for the mold manufacturing process. The fluid microchannels were laid out on the mask in pairs, with one end of each microchannel leading to an exit port, and the other end joining its pairing microchannel at the orifice. All of the microchannels were 100 μm wide and the orifice width at the intersection was also 100 μm wide. Variations could easily be made near the orifice, such as constrictions and turbulence inducers, simply by altering the mask design. Four spots were arranged in a line, with the spotting ports separated by 500 μm gaps. The other ends of the microchannels leading to the exit ports were spaced apart by 5 mm for easy packaging. Only a single orifice embodiment is shown in FIGS. 15, 19, 20 and 22-24 for clarity.

A 76.2 mm single-side polished silicon wafer was used as the substrate for the SU-8 mold. The wafer was preheated for 10 minutes at 95° C. to drive off the water from the surface and improve adhesion. Once the wafer had cooled, SU-8 50 (Microchem) was spun on at 1300 rpm for 60 seconds to produce a 100 μm thick layer. See FIG. 19. The wafer was soft-baked at 65° C. for 3 minutes and 95° C. for 2 hours to cure as much of the photoresist solvent as possible. The microchannel structure had a 1:1 aspect ratio. Following the soft baking process the wafer was cooled in preparation for exposure.

Exposure of the wafer was carried out on a 365 nm light source aligner (EVG), but the exposure process had to be altered to allow the use of the emulsion mask. The mask was laid directly on the wafer in the approximate center with the emulsion side facing the SU-8 and covered with a 101.6 mm glass plate. See FIG. 7. The wafer was then inserted into the aligner and exposed with a 430 mJ/cm2 dosage. Post exposure baking was carried out for 3 minutes at 65° C. for 3 minutes and 95° C. for 15 minutes to complete the cross-linking of the exposed resist. The wafer was immersion developed in propylene glycol monomethyl ether acetate (PG-MEA) (Microchem) for 20 minutes, washed in isopropyl alcohol and dried with a nitrogen spray.

Figure 21:
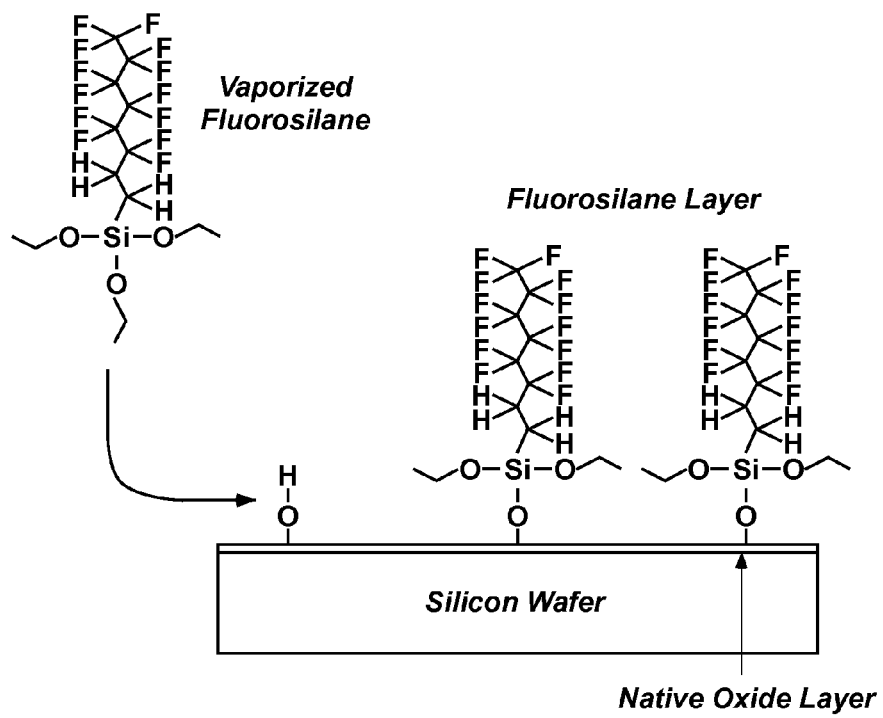
Figure 22:
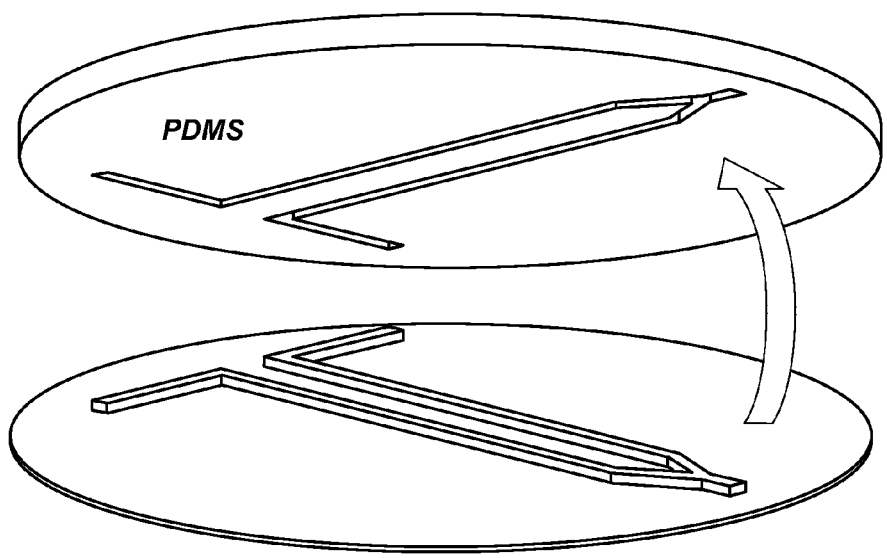
Figure 23:
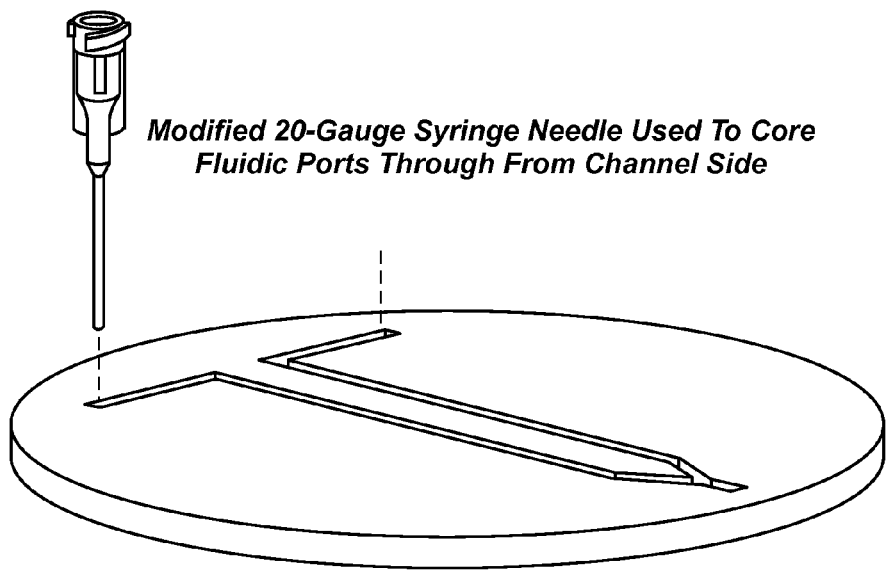
Figure 24:
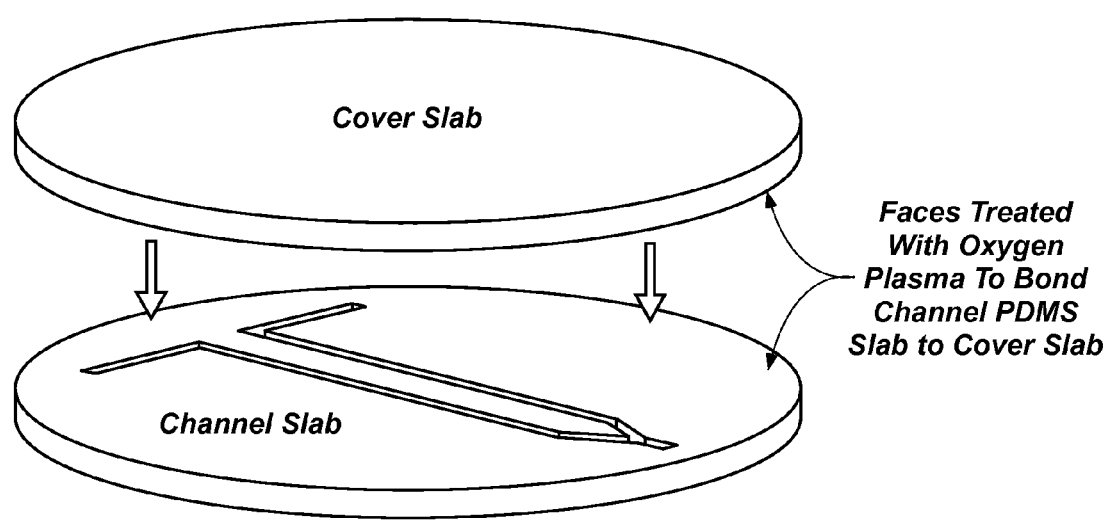

Silicon wafers normally have a thin native oxide layer on the surface which PDMS will bond to strongly, preventing the casting from releasing from the mold. To prevent this the fluorosilanizing agent (tridecafluoro-1,1,2,2-tetrahydrooctyl) triethoxysilane (Gelest) was used to coat to native oxide with a fluorocarbon layer. See FIG. 21. The fluorosilane was evaporated in a vacuum chamber containing the wafer for 2 hours, allowing a surface reaction to occur at a controlled rate and form a monomolecular surface layer. The silane group binds preferentially to the oxide layer, leaving the fluorocarbon residue sticking up from the wafer surface, preventing the PDMS from bonding. A blank 76.2 mm wafer was also coated along with the SU-8 mold to provide a mold for the microchannel cover slab.

4.1.3 PDMS Casting and Curing

PDMS was used as-is from the supplier (Dow Corning), and was used as directed. 40 mL of the base resin was mixed with the curing agent in a 10:1 ratio by volume and mixed thoroughly. The pre-polymer mixture was placed in a vacuum for 1 hour to remove all air bubbles and then split into two equal parts for each of the molds. The pre-polymer was poured over each wafer and allowed to settle evenly. The wafers were then placed in a vacuum for 1 hour to remove any air bubbles trapped between the mold and pre-polymer. Once all air was evacuated from the molds, they were placed in an oven at 65° C. for 2 hours to cure. Immediately after the cure was complete, the castings were peeled from the mold, washed in isopropyl alcohol and dried with a nitrogen spray. See FIG. 22.

4.1.4 Fluidic Port Coring

The PDMS cover slab was placed in a sealed container to prevent dust contamination during the port coring process. The ports were cut in the PDMS microchannel slab from the microchannel side of the casting, making alignment of the holes with the microchannels simple. The coring process was performed using a modified 20-gauge syringe needle that had been modified at the tip to form a sharp, beveled cutting edge. See FIG. 23. This edge allowed the coring tool to make a clean cut into the PDMS, forming a cylindrical hole from the microchannel face of the slab to the outer face of approximately the same diameter as the internal bore of the needle (0.58 mm). To connect existing fluidic systems to the microchannels, an unmodified 20-gauge needle was inserted into the hole, and the appropriate LUER™ connections made to the needle. The seal between the needle and the PDMS is purely mechanical, caused by compression of the smaller hole diameter (0.58 mm) around the larger outer diameter of the needle (0.91 mm). This fluidic connection has proved to be extremely robust, and is capable of withstanding severe mechanical shock and handling, as well as multiple insertions and removals of the needle. Prior to microchannel sealing, the needle connections were removed to allow the PDMS slabs to sit level in the oxygen plasma chamber for surface treatment.

4.1.5 Channel Sealing

To form a hermetic seal between the PDMS microchannel casting and the PDMS cover slab, an oxygen plasma was used to form a thin silicon dioxide layer on the sealing surfaces. See FIG. 24. The oxidized surfaces once pressed together form an immediate hermetic seal, effectively sealing the microchannels. However, this surface treatment must be performed within hours of peeling the PDMS castings from the molds. Both of the PDMS castings were washed again in isopropyl alcohol and dried with a nitrogen spray just prior to placement in the oxygen plasma chamber. The oxygen plasma was run for 45 seconds at 125W RF power and 300 milliTorr chamber pressure with 75 sccm of pure oxygen. Within seconds of removal from the chamber, the oxidized PDMS surfaces were aligned and pressed together, sealing the microchannels. To ensure that the slabs sealed completely, they were clamped together and left at room temperature for a period of two days. Once the sealing process was complete, the slabs were trimmed with a razor blade in preparation for spotter face cutting.

4.1.6 Spotter Face Cutting

The spotter face is defined by the cross-section of the intersection between the fluid microchannel pairs. The four pairs of microchannel intersections were arranged in a line so that all four intersections could be cleaved at once and form the resulting four spots on a single face. See FIG. 15. To make alignment of the cut easier, the intersecting ends of the microchannel pairs were drawn out into a single 100 µm by 100 µm channel approximately 2 mm in length. The cut was made through the microchannel as close to the intersection as possible to minimize the dead volume at the spot face. The exact placement of this cut could have been precisely controlled with aligned blades for repeatable spotter face placement on multiple spotters. Once the spotter face had been cut, the syringe needle fluidic connections were replaced, making the spotter ready for use.

4.1.7 Spotter Operation

Operation of this embodiment of the spotter requires that the spotted surface be relatively clean and smooth to allow the spotter face to form a fluid seal. The spotter face must then be pressed onto the required area and held for the duration of the fluid flow. See FIG. 3. Each microchannel pair is connected at the fluid connection port to a fluid input and output line. Fresh or recirculated fluid is pumped into the fluid inlet and waste/excess fluid is simultaneously pumped out. In higher flow rate depositions, infusing and withdrawing the fluid from the spotter will prevent leakage that can occur if only infusion is used. Multiple layering and washings on the spotted area can be performed simply by changing the fluid that is flowed over the spot. Additionally, the spotter may be used for fluid loading into other microfluidic systems, simply by pressing the spotter face against a surface port array. Surface modification of the internal walls of the microchannel can be performed easily using solutions such as BSA (bovine serum albumin) to reduce build up of materials. However, the spotter could be made cheap enough to be disposable, eliminating contamination issues.

4.2 EXAMPLE II

Spotter fabrication can be a three-stage process. First, PDMS, or any other suitable substance, is used to form a membrane on a mold (such as a lithographically-defined mold). Protrusions in the mold are used to define the spotting holes. This step creates the spotter face. Second, microchannels are formed on a second mold to connect to fluidic interconnects. Third, the microchannel layer is bonded to the backside of the spotter face. Both the spotter face and the microchannel layer are peeled simultaneously from the molds.

The membrane molding process yields a smooth lower surface, making spotter-substrate fluid sealing easier when the substrate is smooth. Fluid flow over each spot is individually controlled and spot shapes, number and arrangement can be customized as necessary. The mold may be adapted so that spotter face seals against uneven substrates, such as micro total analysis systems, biosensors, and transducers.

The spotter face and the spotter conduits can be formed at the same time as in Example I or separately as in Example II. Either way the parts can be molded from a cast, lithographically formed, or formed by some other method.

All references, including publications, patents, and patent applications, cited herein are hereby incorporated by reference to the same extent as if each reference were individually and specifically indicated to be incorporated by reference and were set forth in its entirety herein.

While disclosed with particularity, the foregoing techniques and embodiments are more fully explained and the invention described by the following claims. It is clear to one of ordinary skill in the art that numerous and varied alterations can be made to the foregoing techniques and embodiments without departing from the spirit and scope of the invention. Therefore, the invention is only limited by the claims.

REFERENCES

[1] I. Papautsky et al. *Parallel Sample Manipulation Using Micromachined Pipette Arrays Microfluidic Devices and Systems, Proceedings SPIE*, Vol. 3515 (September 1998), pp. 104-114. TS510.S63x vol. 3515.

[2] Charati et al. *Diffusion of Gases in Silicone Polymers: Molecular Dynamics Simulations, Macromolecules*, Vol. 31 (1998), pp. 5529-5535. QD 380.M2x.

[3] Anderson et al. *Fabrication of Topologically Complex Three-Dimensional Microfluidic Systems in PDMS by Rapid Prototyping, Anal. Chem.*, Vol. 72, no. 14 (Jul. 15, 2000), pp. 3158-3164. TP1.I615.

[4] http://www.invitrogen.com/content.cfm?pageid=10620, downloaded Jun. 30, 2005.

What is claimed is:

1. A spotter for depositing a substance on a surface in an ordered pattern, the spotter comprising: a plurality of fluid pathways, wherein each fluid pathway independently comprises at least first conduit and a second conduit, the first and second conduits each having a proximal and a distal end, the first and second conduits each having a wall defining a channel in the first and second conduits, wherein the distal end of the first conduit and the distal end of the second conduit join to form an orifice, wherein the orifice is adapted to form a seal with a surface, thereby forming a plurality of independent fluid pathways having a plurality of orifices adapted to form a seal with a surface, wherein each fluid pathway is configured such that fluid is flowable in one direction through the first conduit, over the surface, and then through the second conduit when the orifice is sealed against the surface;

the plurality of the orifices configured in a static array adapted to dispose fluid on the surface in an ordered pattern.

2. The spotter of claim 1, wherein a fluid pathway further comprises a third conduit, where the third conduit has a proximal and a distal end, and a wall defining a fluid pathway channel in the third conduit, wherein the distal end of the third conduits is connected to the distal ends of the first and second conduits to form a fluid pathway having three fluid flow channels.

3. The spotter of claim 1, wherein the static array of the plurality of orifices are configured in a chessboard or honeycomb fashion.

4. The spotter of claim 1, wherein two or more of the proximal ends of the first conduits of each of the plurality of independent fluid pathways are interconnected.

5. The spotter of claim 4, wherein two or more of the proximal ends of the second conduits of each of the plurality of fluid pathways are interconnected.

6. The spotter of claim 1, wherein two or more of the plurality of independent fluid pathways are interconnected to become a single fluid pathway.

7. The spotter of claim 1, wherein the plurality of independent fluid pathways are connected to a pump.

8. The spotter of claim 1, further comprising a constriction of at least one of the plurality of fluid pathways.

9. The spotter of claim 1, wherein a junction of the distal end of the first conduit and the distal end of the second conduit is adapted-to provide a turbulent transition flow of a substance over the surface.

10. The spotter of claim 1, further comprising thermal regulatory or gas diffusion elements proximal to the orifices.

11. The spotter of claim 1, wherein the proximal ends of the second conduits are connected to a reservoir.

12. The spotter of claim 1, wherein the proximal ends of the first conduits are connected to one reservoir and the proximal ends of the second conduits are connected to a second reservoir.

13. The spotter of claim 1, wherein each of the proximal ends of the first conduits of each of the fluid pathways are connected to individual reservoirs and the proximal ends of all of the second conduits are connected to a second individual reservoir.

* * * * *